US007358987B2

(12) United States Patent
Takeshige et al.

(10) Patent No.: US 7,358,987 B2
(45) Date of Patent: Apr. 15, 2008

(54) ENDOSCOPE SYSTEM

(75) Inventors: Masaru Takeshige, Tokyo (JP); Hiroyuki Kobayashi, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 397 days.

(21) Appl. No.: 10/093,500

(22) Filed: Mar. 11, 2002

(65) Prior Publication Data
US 2002/0126204 A1 Sep. 12, 2002

(30) Foreign Application Priority Data
Mar. 12, 2001 (JP) ............................. 2001-069495

(51) Int. Cl.
H04N 7/18 (2006.01)

(52) U.S. Cl. ........................... 348/74; 348/45; 348/65; 348/77; 348/79; 600/117; 600/109; 600/114; 600/101; 600/160; 600/178

(58) Field of Classification Search ................. 348/74, 348/45, 65, 77, 79; 600/101, 117, 109, 114, 600/160, 178
See application file for complete search history.

(56) References Cited

U.S. PATENT DOCUMENTS

| 4,611,271 | A | * | 9/1986 | Hattori et al. ................ 700/79 |
| 5,022,382 | A | * | 6/1991 | Ohshoji et al. ............. 600/156 |
| 5,164,824 | A | * | 11/1992 | Ieoka et al. .................... 348/71 |
| 6,078,681 | A | * | 6/2000 | Silver .......................... 382/133 |
| 6,436,032 | B1 | * | 8/2002 | Eto et al. ..................... 600/117 |
| 6,682,479 | B1 | * | 1/2004 | Takahashi et al. .......... 600/159 |

* cited by examiner

Primary Examiner—Shawn S. An
(74) Attorney, Agent, or Firm—Greenblum & Bernstein, P.L.C.

(57) ABSTRACT

An endoscope system is provided with an endoscope processor that processes an image signal output by an electronic endoscope, an endoscope controlling system connected to the endoscope processor to control operation of the endoscope processor or a device connected to the endoscope processor, an endoscope server that communicates with the endoscope controlling system through a first network, a service server that communicates with at least one of the endoscope processor and the device connected to the endoscope processor through a second network, and a surveillance circuit that surveys operation of the endoscope processor or the device connected to the endoscope processor, the endoscope controlling system transmits a surveying result to the endoscope server through the first network, and the endoscope server transmits the surveying result of the surveillance circuit to the service server through the second network.

15 Claims, 21 Drawing Sheets

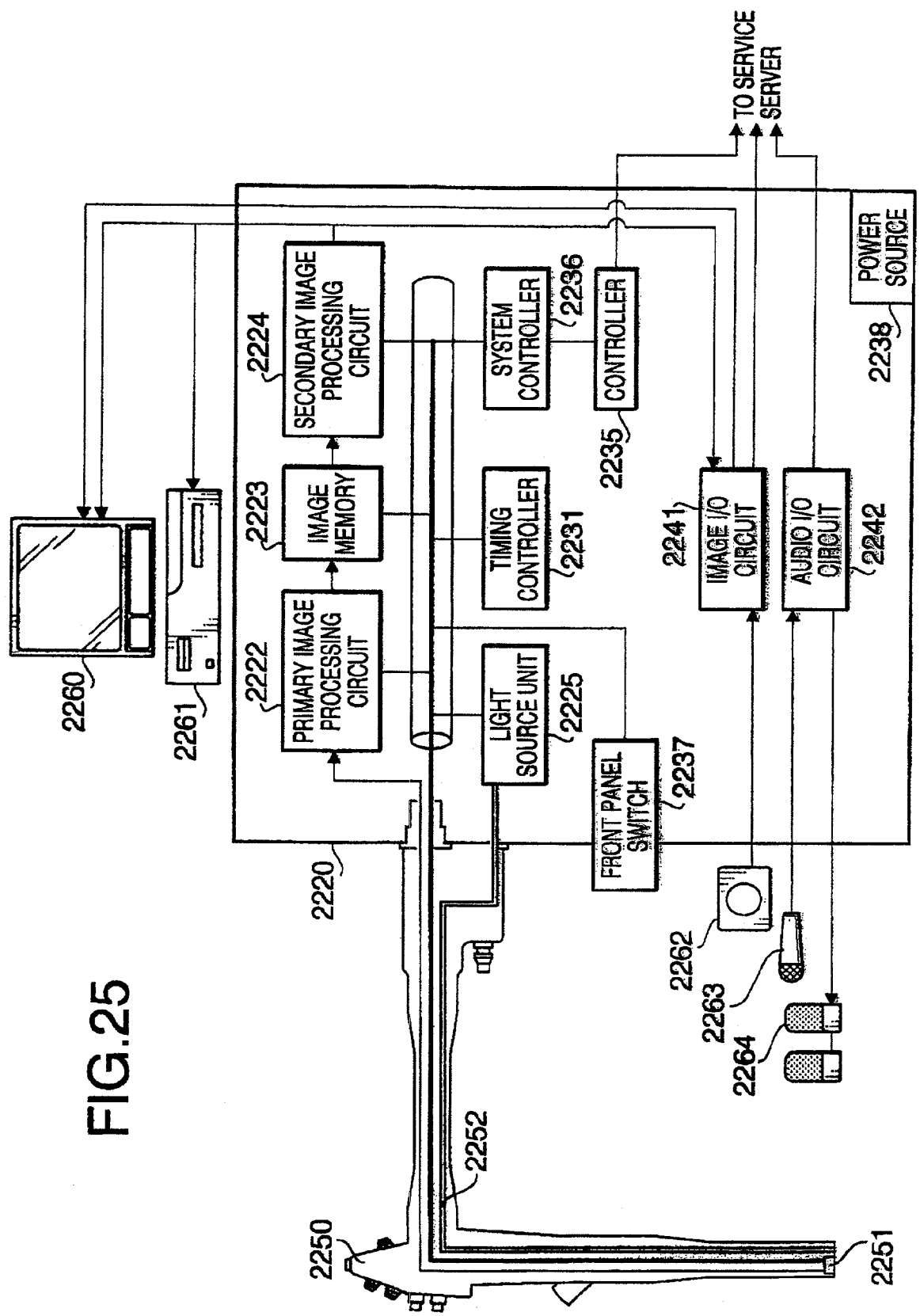

ENDOSCOPE SYSTEM

BACKGROUND OF THE INVENTION

The present invention relates to an endoscope system including an electronic endoscope, and a processor that processes an image signal output by the electronic endoscope and transmits the processed image signal to a displaying device.

Conventionally an electronic endoscope provided with an image capturing element such as a CCD (Charge Coupled Device) at a tip portion thereof IC used in association with a processor which processes an image signal output by the image capturing element and outputs the processed signal to an outputting device such as a display or a video printer.

Such a processor is generally provided with an illumination device which emits light for illuminating an object to be observed to a light guide for the electronic endoscope. Typically, such a processor employs a so-called surface-sequential method for obtaining a color image. That is, such a processor is provided with an illumination device that emits three beams having three primary colors RGB (Red, Green and Blue) sequentially at a predetermined interval to illuminate the object, and the processor synthesized the images corresponding to the three colors RGB to generate a color image.

Such an electronic endoscope and processor are provided with electronic devices such as an image capturing element, image processing device, a precise mechanism such as a filter mechanism for generating three color components sequentially, and expendable supplies such as a lamp. Therefore, maintenance of the electronic endoscope system is generally performed by a trained person periodically.

Generally, however, one trained person is required to perform maintenance jobs for a plurality of endoscope systems. When the endoscope at remote areas area subjected to the maintenance, the trained person may be required to visit the remote area, which increases maintenance cost of the endoscope system. Further, in such a system, when a problem occurs, it is very difficult to fix the same promptly.

SUMMARY OF THE INVENTION

In view of the above, the present invention is intended to provide an endoscope system with which the maintenance can be done quickly even though the endoscope system is located in remote areas.

In view of the above, there is provided an endoscope system, which is provided with an endoscope processor that processes an image signal output by an electronic endoscope and outputs a processed image signal to an image outputting system, an endoscope controlling system that is connected to the endoscope processor and controls operation of at least one of the endoscope processor and a device connected to the endoscope processor, an endoscope server that communicates with the endoscope controlling system through a first network, a service server that communicates with at least one of the endoscope processor and the device connected to the endoscope processor through a second network, and a surveillance circuit that surveys operation of at least one of the endoscope processor and the device connected to the endoscope processor, the surveillance circuit being provided in the endoscope controlling system. The endoscope controlling system transmits a surveying result of the surveillance circuit to the endoscope server through the first network, and the endoscope server transmits the surveying result of the surveillance circuit to the service server through the second network.

With this configuration, the operation condition of the endoscope processor and/or devices connected thereto can be monitored at the service server, which may be located remote from the respective endoscope processors and/or connected devices.

In a particular case, the surveillance circuit may be configured to detect an irregular condition of at least one of the endoscope processor and the device connected to the endoscope processor.

Optionally, the device connected to the endoscope processor includes the electronic endoscope.

In some embodiments, a communication between the service server and the endoscope server is established only when authentication is confirmed therebetween.

Optionally or alternatively, a communication between the endoscope server and the endoscope controlling system should be established only when authentication is confirmed therebetween.

Still optionally, at least one of the endoscope processor and the service server may include an image input system, at least the other of the endoscope system and the service server may include an image output system, and an image input through the image input system is transmitted to the image output system through the second network.

Optionally or alternatively, at least one of the endoscope processor and the service server may include an audio input system, at least the other of the endoscope processor and the service server may include an audio output system, and an audio input through the audio input system is transmitted to the audio output system through the second network.

According to another aspect, there is provided an endoscope system, which is provided with an endoscope processor that processes an image signal output by an electronic endoscope and outputs a processed image signal to an image outputting system, an endoscope controlling system that is connected to the endoscope processor and controls operation of at least one of the endoscope processor and a device connected to the endoscope processor, an endoscope server that communicates with the endoscope controlling system through a first network, and a service server that communicates with at least one of the endoscope processor and the device connected to the endoscope processor through a second network. Further, the endoscope controlling system includes a system controller that executes a program controlling operation of the endoscope processor, and a controller that controls the system controller to modify the program executed by the system controller. In this case, the service server may be configured to transmit data used for modifying the program to be executed by the system controller to the endoscope server through the second network, and the endoscope server may transmit the data transmitted from the service server to the endoscope controlling system through the first network. The controller of the endoscope controlling system controls the system controller to modify the program to be executed by the system controller in accordance with the data transmitted from the endoscope server.

According to a further aspect, there is provided an endoscope system, which is provided with an endoscope processor that processes an image signal output by an electronic endoscope and outputs a processed image signal to an image outputting system, an endoscope controlling system that is connected to the endoscope processor and controls operation of at least one of the endoscope processor and a device connected to the endoscope processor, a service server that communicates with at least one of the endoscope process or and the device connected to the endoscope processor through a predetermined network, and a surveillance circuit that surveys operation of at least one of the endoscope processor and the device connected to the endoscope processor, the surveillance circuit being provided in the endoscope controlling system. With this configuration; the endoscope controlling system is configured to transmit a surveying result of the surveillance circuit to the service server through the predetermined network.

According to another aspect, there is provided an endoscope system, which is provided with an endoscope processor that processes an image signal output by an electronic endoscope and outputs a processed image signal to an image outputting system, an endoscope controlling system that is connected to the endoscope processor and controls operation of at least one of the endoscope processor and a device connected to the endoscope processor, a service server that communicates with at least one of the endoscope processor and the device connected to the endoscope processor through a second network. With this configuration, the endoscope controlling system may include a system controller that executes a program controlling operation of the endoscope processor, and a controller that controls the system controller to modify the program executed by the system controller. The service server is configured to transmit data used for modifying the program to be executed by the system controller to the endoscope processor through the second network, and the controller of the endoscope controlling system controls the system controller to modify the program to be executed by the system controller in accordance with the data transmitted from the service server.

BRIEF DESCRIPTION OF THE ACCOMPANYING DRAWINGS

FIG. 1 schematically shows an entire configuration of an endoscope system according to a first embodiment of the invention;

Figure 18:
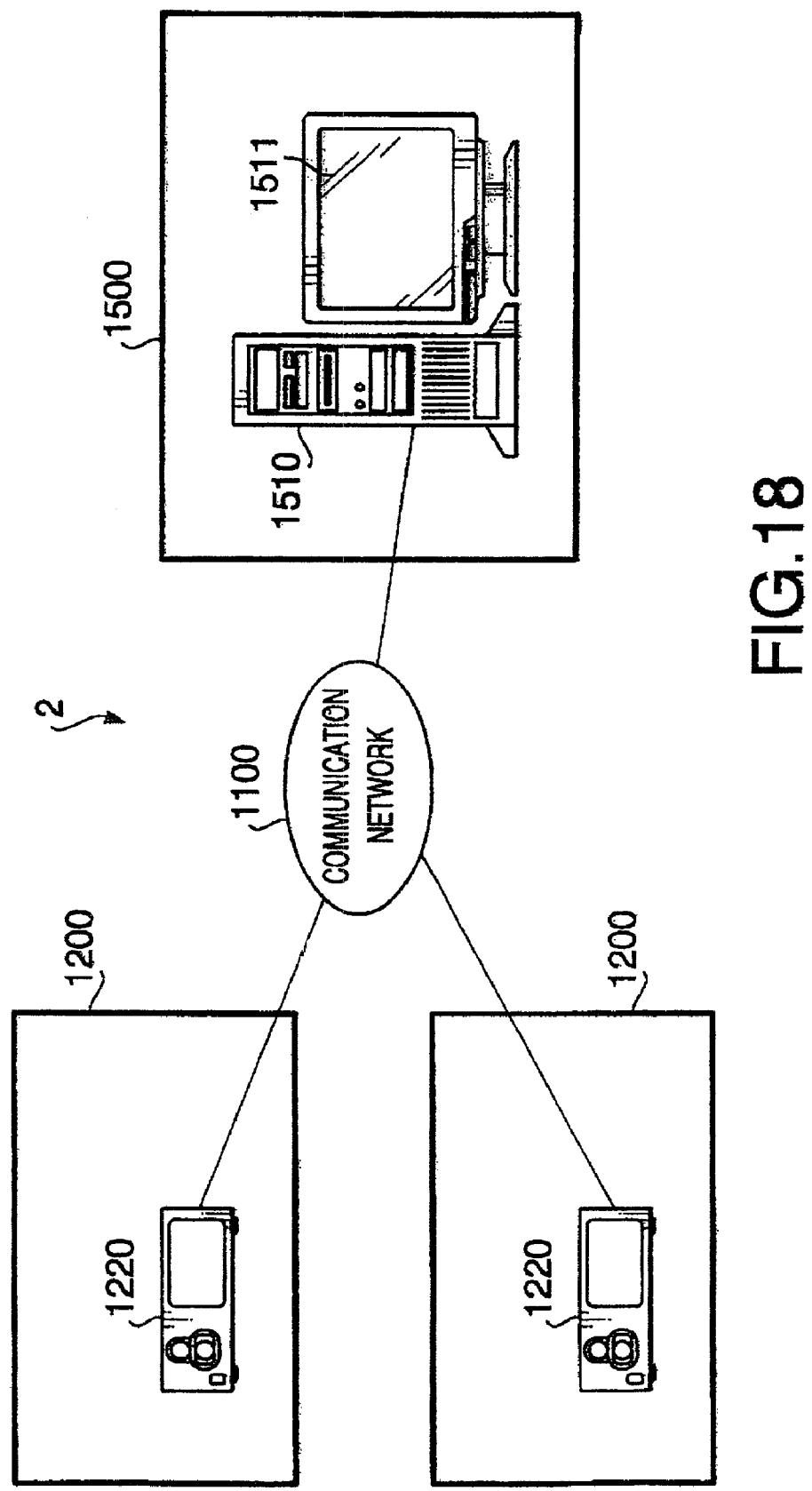
Figure 19:
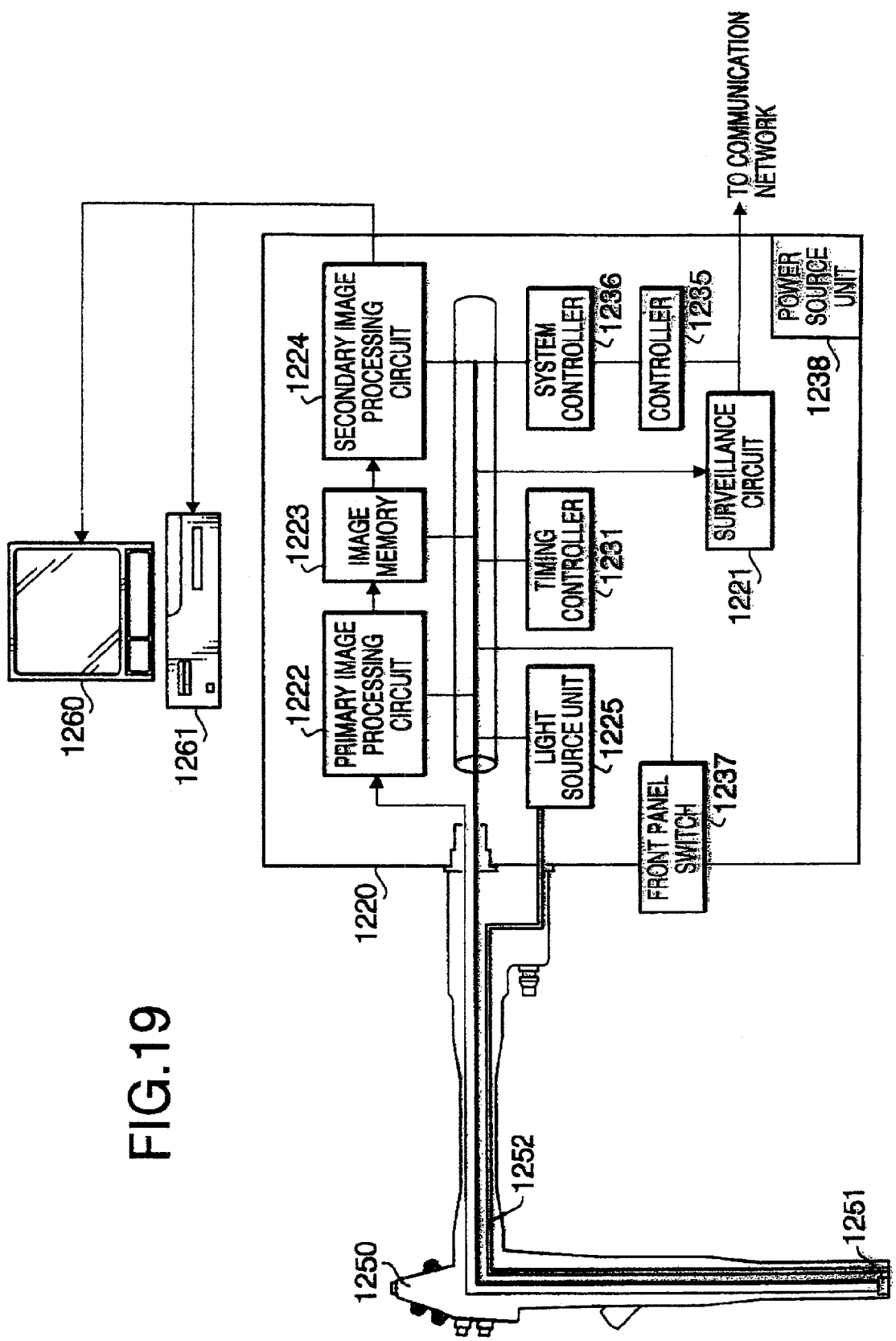
Figure 20:
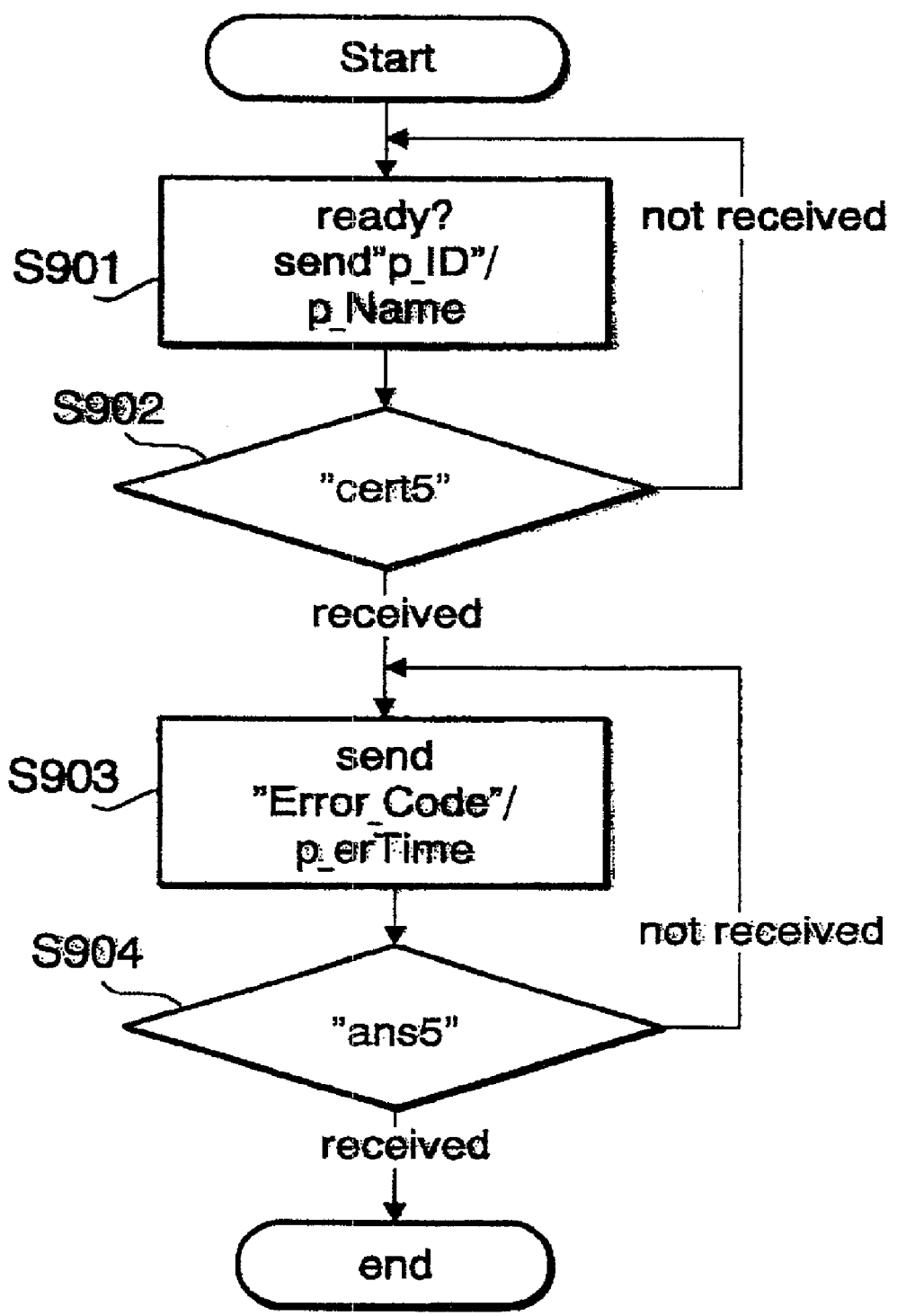
Figure 21:
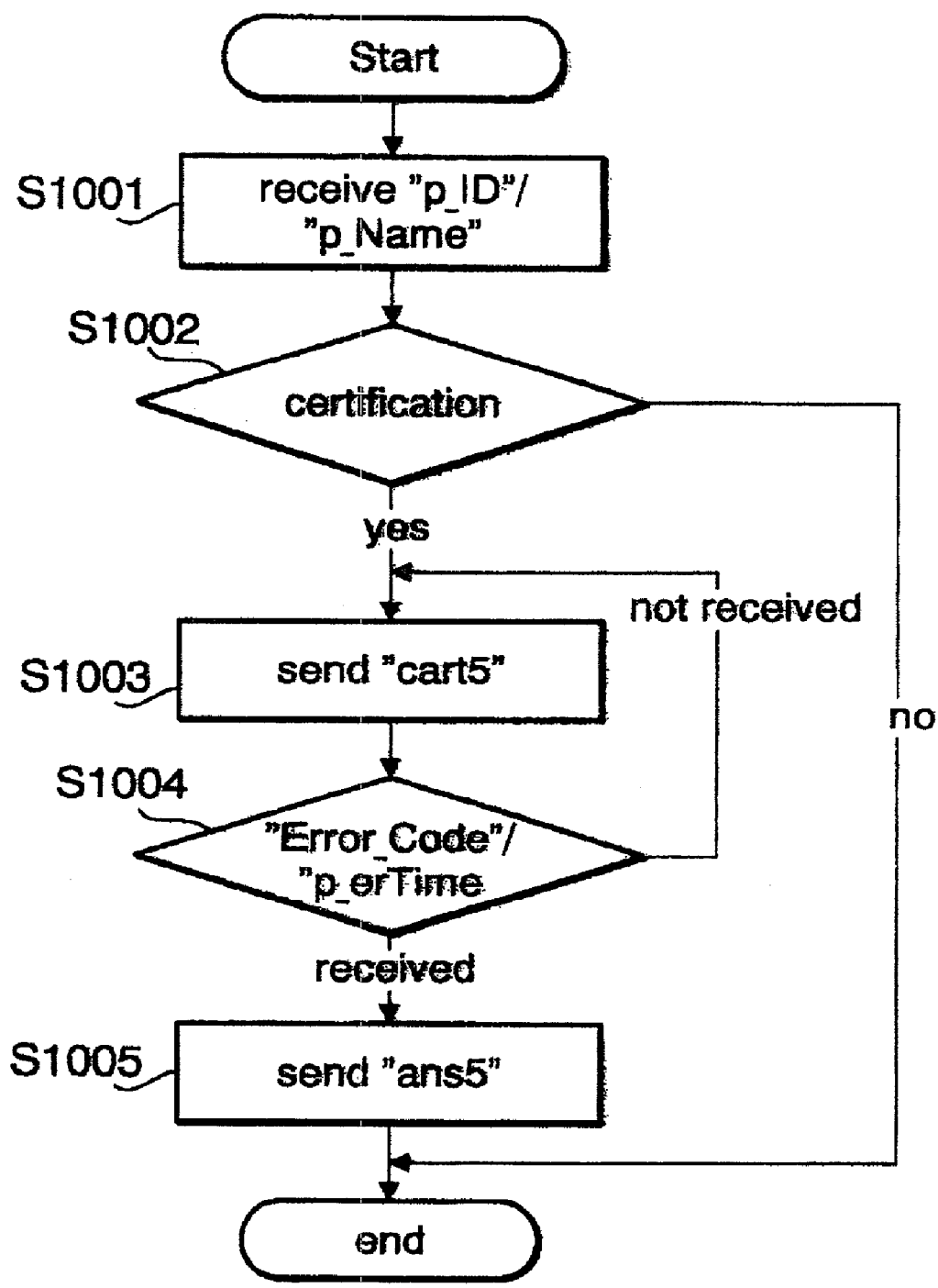
Figure 22:
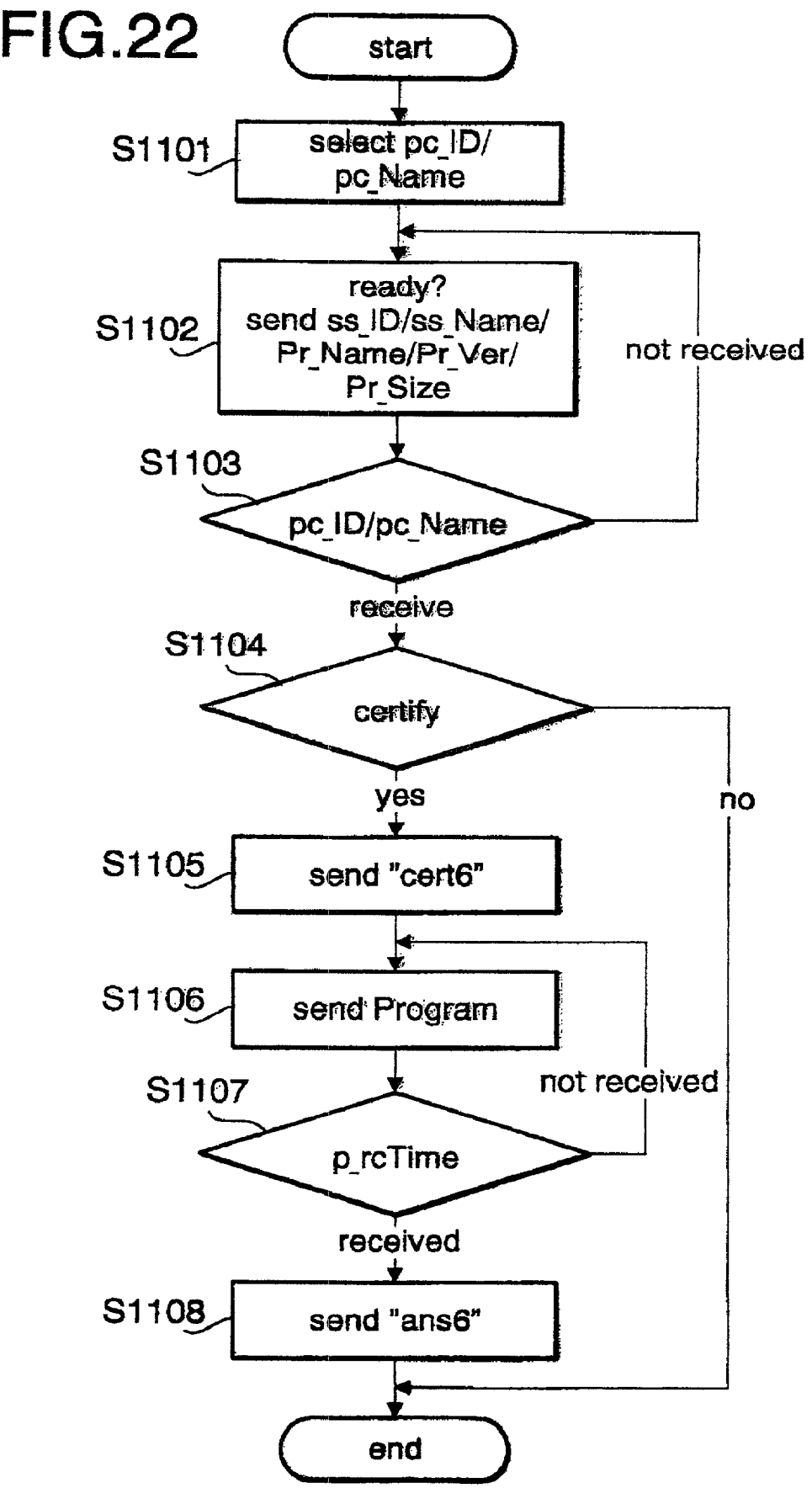
Figure 23:
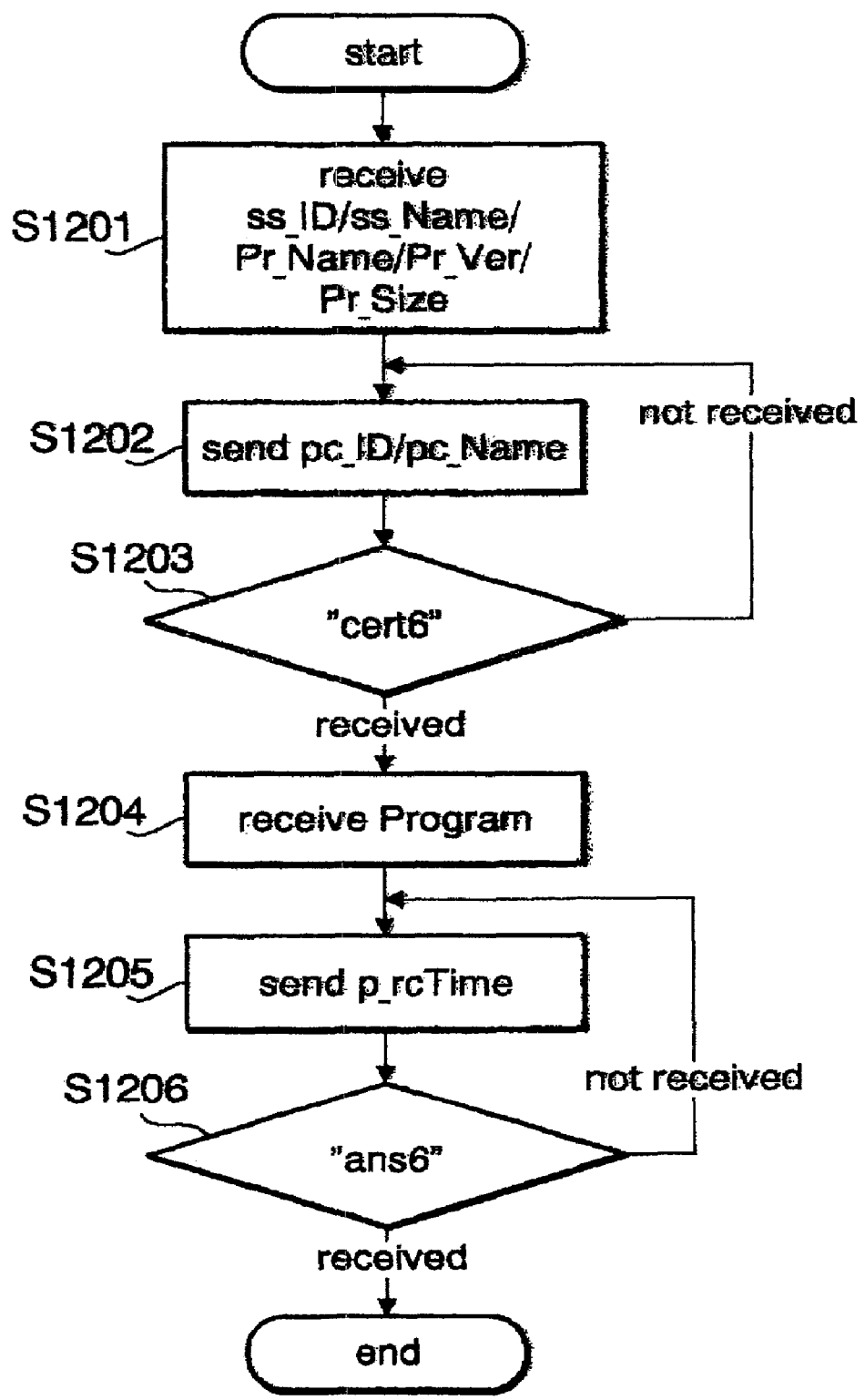
Figure 24:
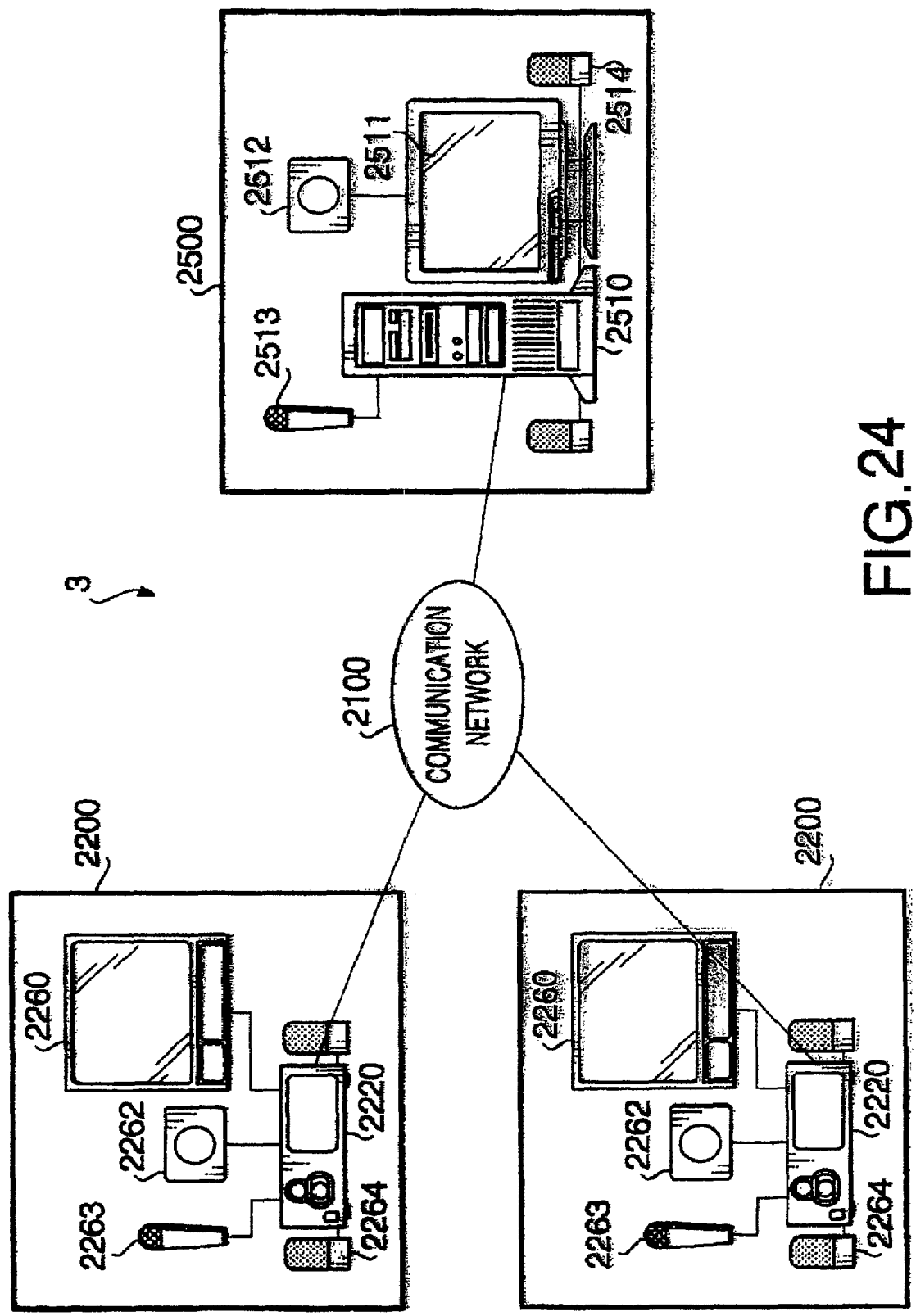

FIG. 18 schematically shows an entire configuration of an endoscope system according to a second embodiment of the invention;

FIG. 19 shows a block diagram of an endoscope processor to which an endoscope is connected;

FIG. 20 is a flowchart illustrating a condition notifying procedure of an endoscope processor, according to the second embodiment;

FIG. 21 is a flowchart illustrating a condition notifying procedure of a service server, according to the second embodiment;

FIG. 22 is a flowchart illustrating a program transmitting procedure of the service server, according to the second embodiment;

FIG. 23 is a flowchart illustrating a program receiving procedure of an endoscope processor, according to the second embodiment;

FIG. 24 schematically shows an entire configuration of an endoscope system according to a third embodiment of the invention; and FIG. 25 shows a block diagram of an endoscope processor to which an endoscope is connected.

DESCRIPTION OF THE EMBODIMENTS

Hereinafter, endoscope systems according to embodiments of the invention will be described with reference to the accompanying drawings.

First Embodiment

Figure 1:
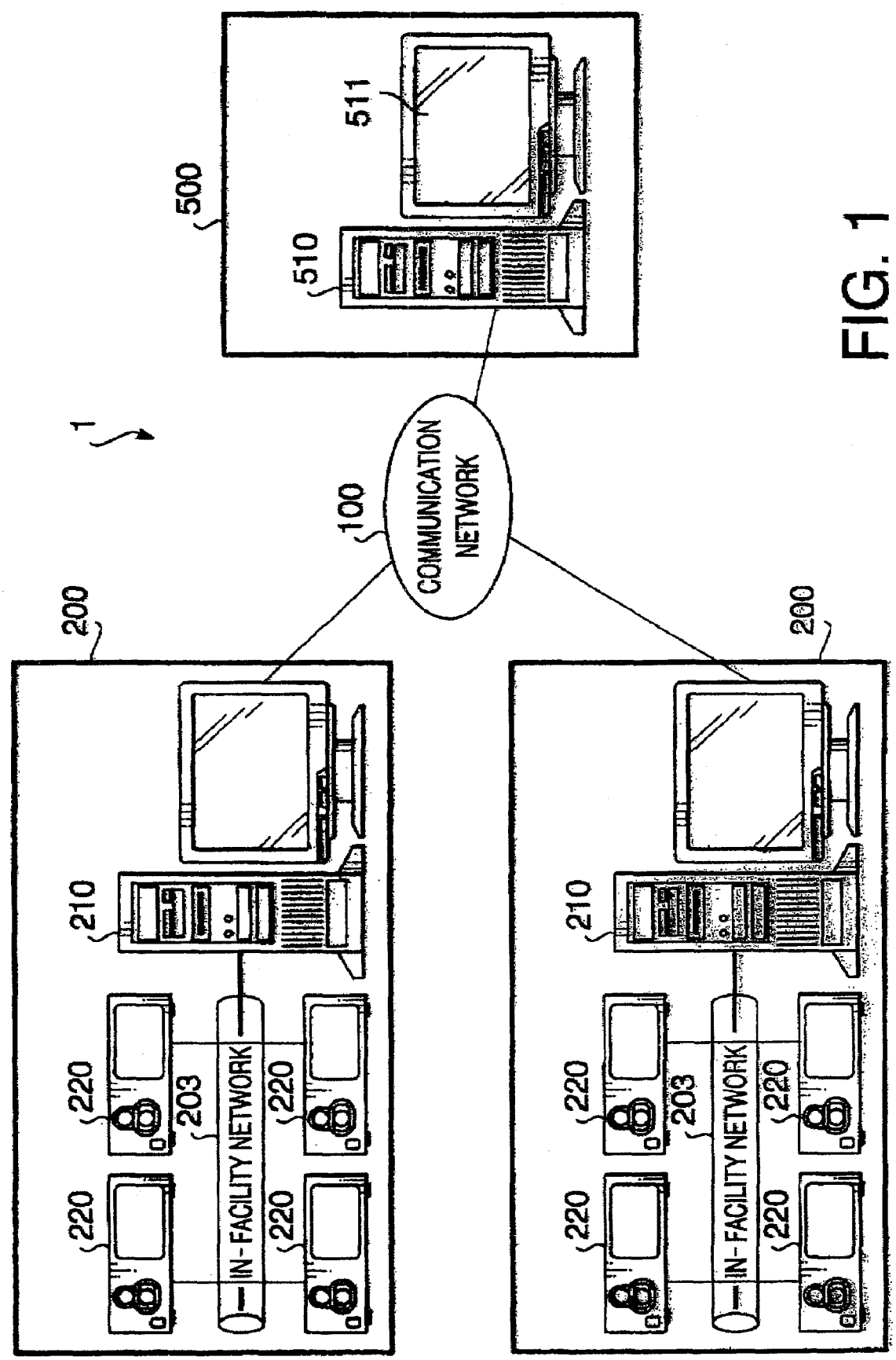

FIG. 1 schematically shows an entire configuration of an endoscope system 1 according to a first embodiment of the invention. The endoscope system 1 includes a service server 510 equipped in a service facility 500, at least one endoscope processor 220 provided in at least one medical facility 200, and at least one endoscope server 210 for surveying condition of the endoscope processor 220. The endoscope server 210 is also equipped in each of the medical facility 200. The endoscope processor(s) 220 and the endoscope server 210 in each medical facility 200 are connected through a in-facility network (Local Area Network) 203.

The endoscope server 210 and the service server 510, which is provided in the service facility 500, are connected through a communication network 100 such as the Internet.

When irregular conditions are encountered in the endoscope processor 220, the endoscope processor 220 notifies the condition to the endoscope server 210 through the in-facility network 203. Then., the endoscope server 210 starts communicating with the communication network 100, and transmits information regarding the irregular conditions of the endoscope processor 220 to the service server 510.

The service server 510 receives the information from the endoscope server 210 and monitor the conditions of each endoscope processor 220. When the service server 510 receives the information notifying the irregular condition of the endoscope processor 220, a message indicative of the irregular condition is displayed on the monitor 511 to notify the same to a service person standing-by in the service facility 500. It should be noted that, in each of above communication/transmission process, an authentication procedure may preferably be included to avoid unauthorized accesses.

The service server 510 is configured to transmit programs to each endoscope server 210 via the communication network 100. With this configuration, the programs determine the operation of the endoscope processor 220 at the service facility 500. At this stage, the endoscope server 210, which received the programs transmitted from the service server 510, transmits the received programs to the endoscope processor 220 connected therewith. The endoscope processor 220 changes its operation when the programs are transmitted from the endoscope server 210.

In each of the above procedures, it is preferable that authentication is performed to avoid the unauthorized access.

As described above, according to the first embodiment, by employing the endoscope processor 220, the traffic of the network is reduced, and therefore, the communication cost for the communication from the service server 510 to the endoscope server 210 is reduced.

Figure 2:
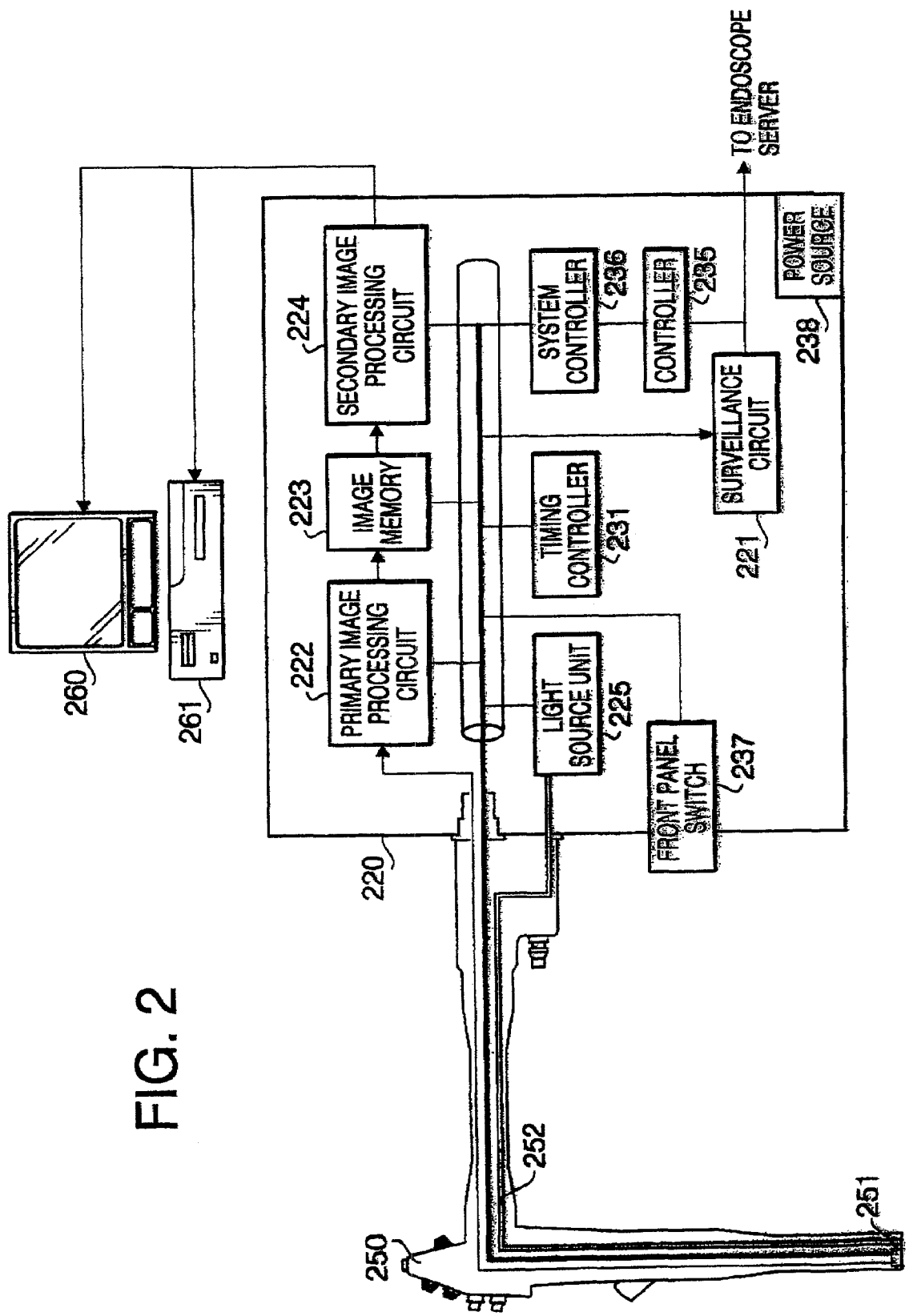
FIG. 2 shows a block diagram of a processor to which an endoscope is connected.

FIG. 2 shows a block diagram of the endoscope processor 220 to which an electronic endoscope 250 is connected. In the first embodiment, inside the endoscope processor 220, a primary image processing circuit 222 which converts the image signal output by a CCD (Charge Coupled Device) 251 into digital data having a predetermined format, and an image memory 223 which stores the digital data output by the primary image processing circuit 222, and secondary image signal processing circuit 224 which converts the digital data stored in the image memory 223 into a video signal such as an NTSC format video signal are provided.

With this configuration, the image captured by the CCD 251 provided in the electronic endoscope 250 can be output as an image displayed on the monitor 260 and/or an image printed out by a video printer 261 connected to the endoscope processor 220.

Further, the endoscope processor 220 includes a light source unit 225 which supplies illumination light to a light guide provided in the electronic endoscope 250, a timing controller 231 which generates synchronizing signals to be supplied to various circuits, and a system controller 236 that controls the respective circuits. The endoscope processor 220 further includes a controller 235 which is connected with the in-facility network 203 to communicate with the endoscope server 210 in order to control the endoscope system controller 236.

Using front panel switches 237, the endoscope processor 220 can be operated. An power unit 238 is provided to supply electrical power to the endoscope processor 220.

The endoscope processor 220 is provided with a surveillance circuit 221. The surveillance circuit 221 examines whether each circuit operates correctly. If the surveillance circuit 221 detects that an irregular operation is performed, it transmits the authentication thereof and the status of the irregular operation to the endoscope server 210 via the in-facility network 203. It should be noted that the irregular operation of the endoscope processor 220 includes, for example, a loss of synchronism of the RGB wheel, or insufficient light amount of a lamp of the light source unit 225.

Figure 3:
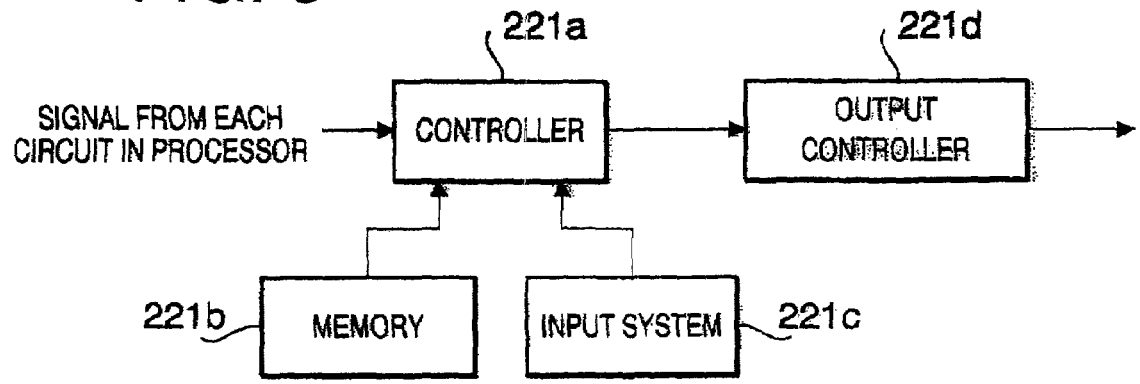
FIG. 3 is a block diagram showing a surveillance circuit implemented in the processor according to the first embodiment.

FIG. 3 is a block diagram showing the surveillance circuit 221 implemented in the endoscope processor 220.

The surveillance circuit 221 includes a controller 221$a$, a memory 221$b$, an input system 221$c$ and an output system 221$d$. A signal indicative of the operation status is transmitted from each circuit in the endoscope processor 220 to the controller 221$a$. Each signal is examined, and when the irregular status is found, the output system 221$d$ outputs the information indicating the irregular status to the endoscope server 210 in accordance with a predetermined transmission protocol. When the irregular status is output from the output system 221$d$, the authentication thereof is also output.

The memory 221$b$ is connected to the controller 221$a$. Information such as a total operation period of the lamp or the like can be stored in the memory 221$b$. Further, the input system 221$c$ is connected with the controller 221$a$. When the lamp is exchanged to a new one, for example, the total operation time stored in the memory 221$b$ should be reset. For such a case, the controller 221$a$ is configured to receive a reset signal through the input system 221$c$. The input system 221$c$ may typically include a keyboard.

Figure 4:
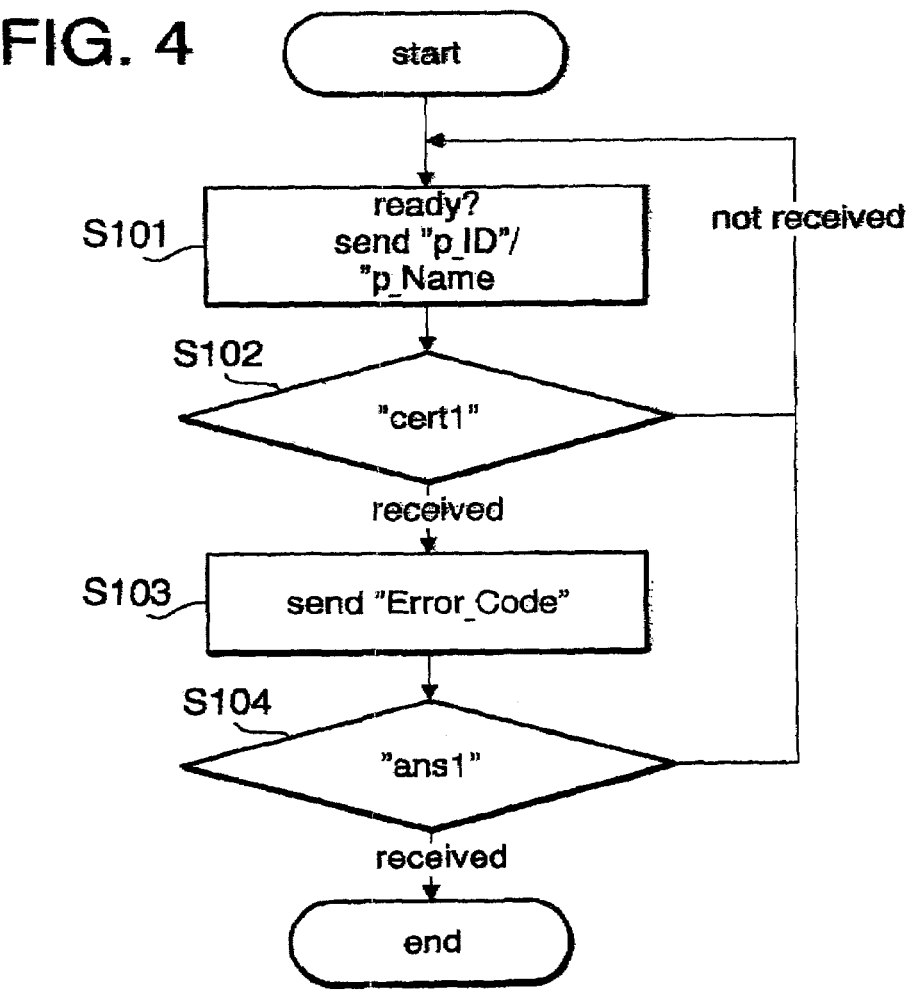
FIG. 4 is a flowchart illustrating a condition notifying procedure of the processor according to the first embodiment.

FIG. 4 is a flowchart illustrating a condition notifying procedure of the endoscope processor 220.

In S101, in the surveillance circuit 221 of each endoscope processor 220, a communication with the endoscope server 210 is established, and then ID number (p_ID) and name (p_Name) are sent for authentication. Then, control proceeds to S102.

In S102, the endoscope processor 220 waits for reception of an authentication code (cert1) from the endoscope server 210. If the authentication code (cert1) is received (S102: received), control goes to S103. If the authentication code (cert1) is not received within a predetermined period (S102: not received), control returns to S101.

In S103, a current irregular condition code (Error_Code) is transmitted. In S104, control waits for reception of a flow end code (ans1) from the endoscope server 210. When the flow end code is received (S104:received), control terminates the procedure shown in FIG. 4. At this stage, it is possible to register data to constitute/update a data base. If the flow end code is not received within a predetermined period (S104:not received), control returns to S101.

It may be convenient to set a predetermined timeout period for the execution of the procedure shown in FIG. 4, and if the loop of S101 to S104 is repeated for a period longer than the timeout period, the flowchart shown in FIG. 4 is forcibly terminated, and a log is recorded.

Figure 5:
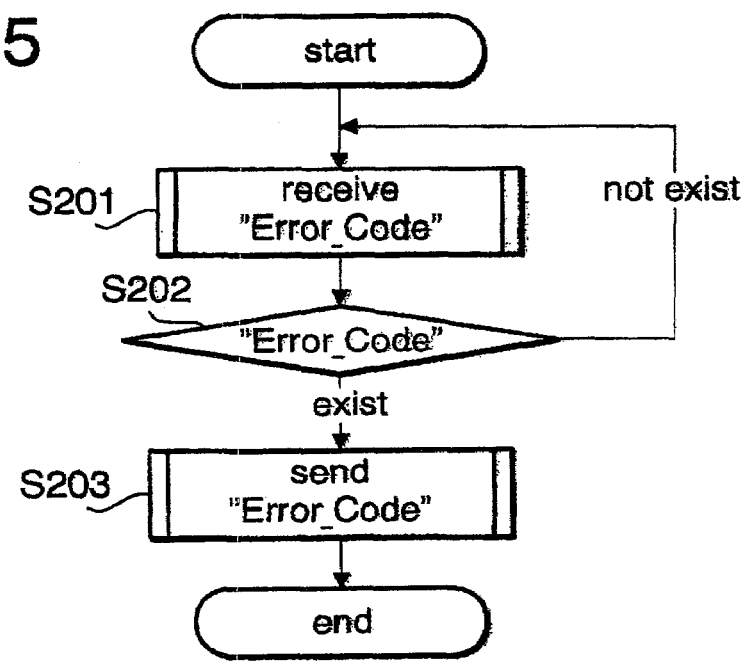
FIG. 5 is a flowchart illustrating a condition notifying procedure of an endoscope server according to the first embodiment.

FIG. 5 is a flowchart illustrating a condition notifying procedure of the endoscope server 210.

In S201, the irregular condition code from the surveillance circuit of each endoscope processor 220 is received. In S202, whether the irregular condition code is correctly received from each surveillance circuit 221 is checked. If the irregular condition code is received correctly (S202:exist), control goes to S203. If the irregular condition code is not received correctly (S202:not exist), control returns to S201.

In S203, the received irregular condition code is transmitted to the service server 510.

Figure 6:
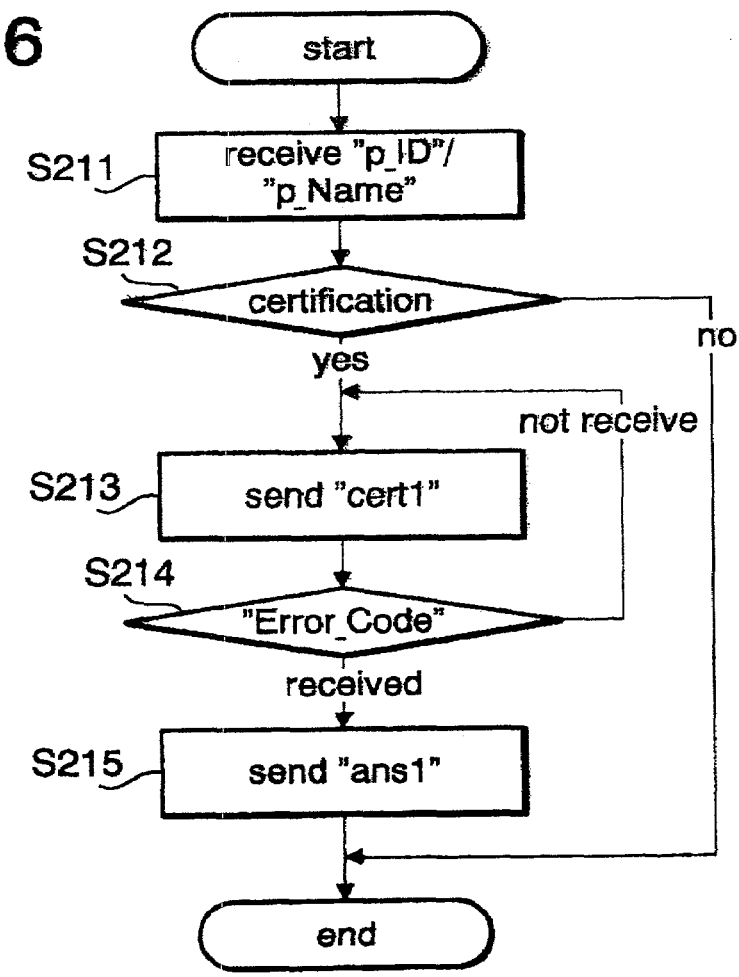
FIG. 6 is a flowchart illustrating a procedure at S201 of FIG. 5.

FIG. 6 is a flowchart illustrating a procedure in S201 of FIG. 5 in detail. In S211, control receives the ID number (p_ID) and the name (p_Name) from the surveillance circuit 221 of the endoscope processor 220. In S212, authentication of the transmitted data is executed. If the authentication is confirmed (S212:yes), control goes to S213. If the authentication is failed or incorrect data is received (S212:no), the procedure shown in FIG. 6 is terminated.

In S213, information (cert1) indicating that the authentication is confirmed is transmitted to the surveillance circuit 221. In S214, the irregular condition code (Error_Code) from the surveillance circuit 211 is received. If the irregular condition code is received in accordance with a predetermined format, control goes to S215. If the irregular condition code having the predetermined format is not received, control returns to S213 and re-transmits the information (cert1) indicating that the authentication is confirmed to the surveillance circuit 221.

In S215, control transmits information (ans1) indicating that the data is received to the surveillance circuit 221. Then, the procedure shown in FIG. 6 is terminated.

Figure 7:
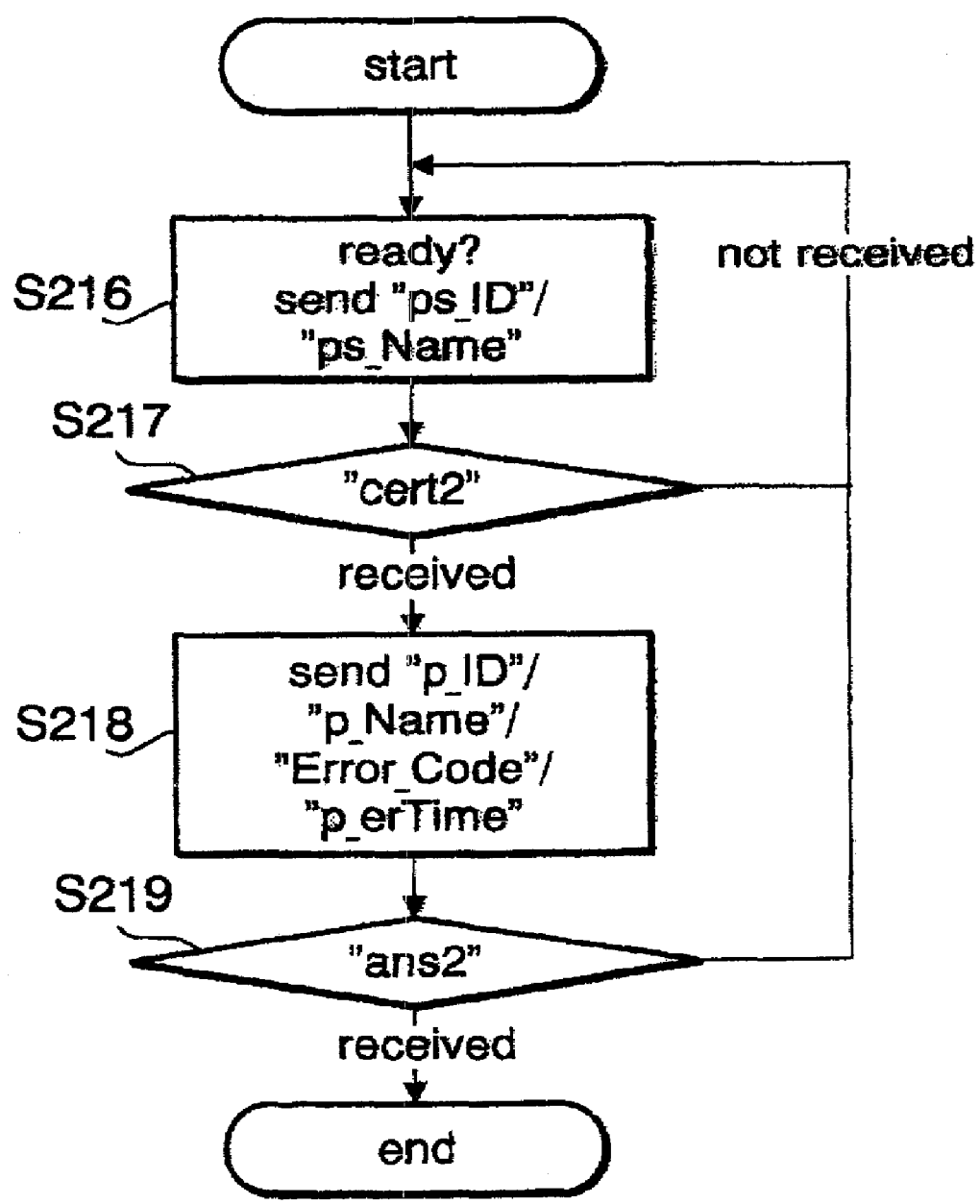
FIG. 7 is a flowchart illustrating a procedure at S203 of FIG. 5.

FIG. 7 is a flowchart illustrating a procedure in S203 of FIG. 5 in detail.

In S206, a communication is established with respect to the service server 510, and authentication through the ID (ps_ID) and the name (ps_Name,) is performed. Then, control proceeds to S217.

In S217, if an authentication code (cert2) is received from the service server 510 (S217:receive), control goes to S218. If the authentication code (cert2) is not received within a predetermined period (S217:not received), control returns to S216.

In S218, the ID (p_ID), the name (p_Name), the irregular condition code. (Error_Code), and the date and time (p_er-Time) when the endoscope server 210 sends the irregular condition code to the service server 510, are received at the service server 510.

In S219, if the flow end code (ans2) is received from the service server 510 within a predetermined period, control terminates the flowchart shown in FIG. 7. It is convenient if the received data is registered and organized as a database. If the flow end code is not received within the predetermined period, control returns to S216.

The procedure shown in FIG. 7 may be modified such that in each of loops S216-S217 and S216-S219 a time out period may be set and if each loop is executed for a period longer than the time out period, a log is recorded and the flowchart may be terminated.

Figure 8:
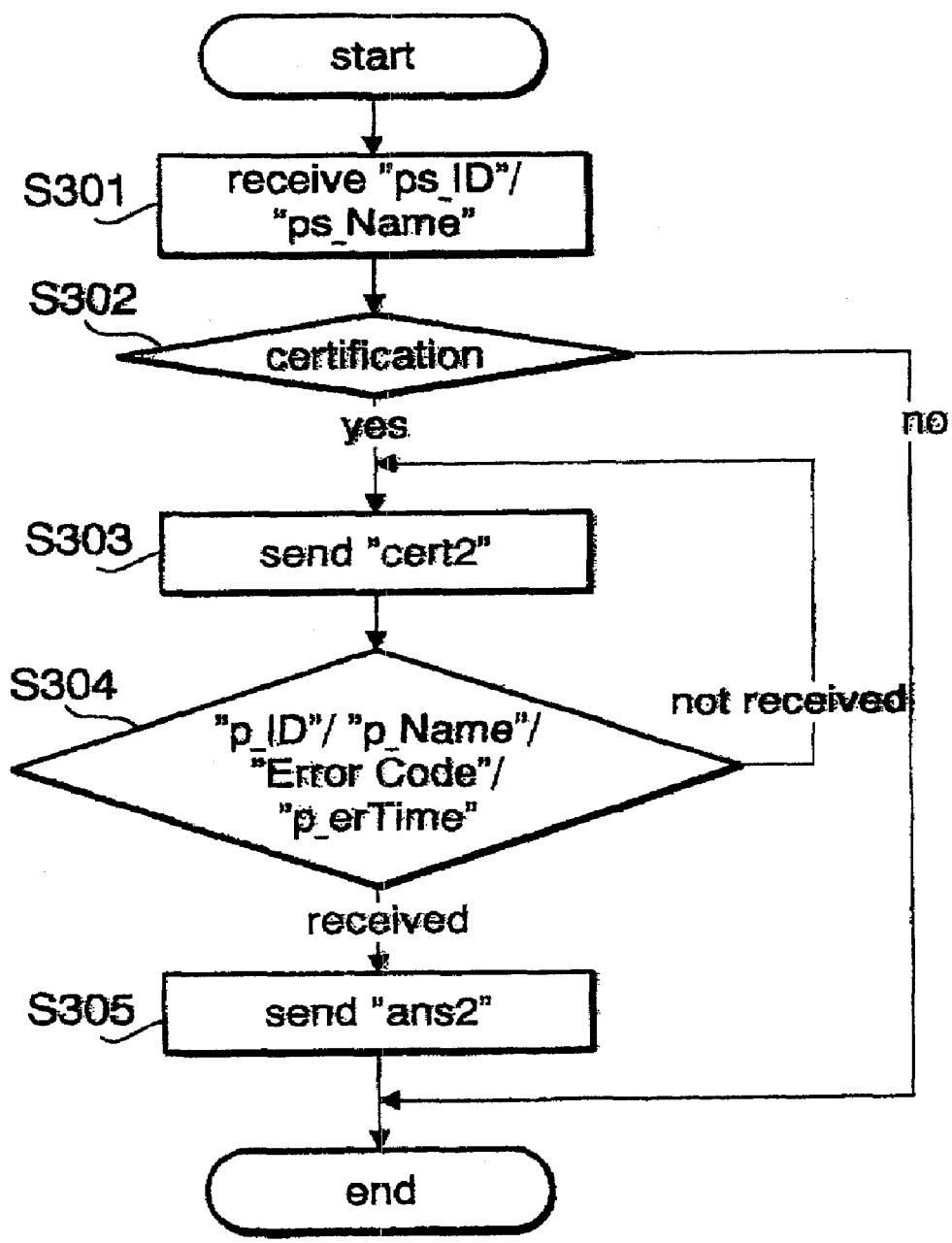
FIG. 8 is a flowchart illustrating a condition notifying procedure of a service server according to the first embodiment.

FIG. 8 is a flowchart illustrating a condition notifying procedure of a service server 510.

In S301, the ID (ps_ID) and the name (ps_Name) of a processor in the irregular condition are received from the endoscope server 210. Then, control goes to S302.

In S302, the communication is established, and the authentication is confirmed. If the authentication is confirmed (S302:yes), control goes to S303. If the communication is not established or the authentication is denied (S302:no), the procedure shown FIG. 8 is terminated.

In S303, data (cert2) indicating that the authentication is confirmed is transmitted to the endoscope server 210. Then, in S304, the ID (p_ID), the name (p_Name), the irregular condition code (Error_Code), and the date and time (p_er-Time) when the endoscope server 210 received the irregular condition code are received. If the above data is received in accordance with a predetermined format (S304:received), control goes to S305. If the data is not received (S304:not received), control returns to S303.

In S305, data (ans2) indicating the reception of the data is transmitted to the endoscope server 210. It is convenient if the received data is registered and organized as a database.

The procedure shown in FIG. 8 may be modified such that a time out period may be set for the loop of S303-S304, and if the loop is executed for a period longer than the time out period, a log is recorded and the flowchart may be terminated.

Figure 9:
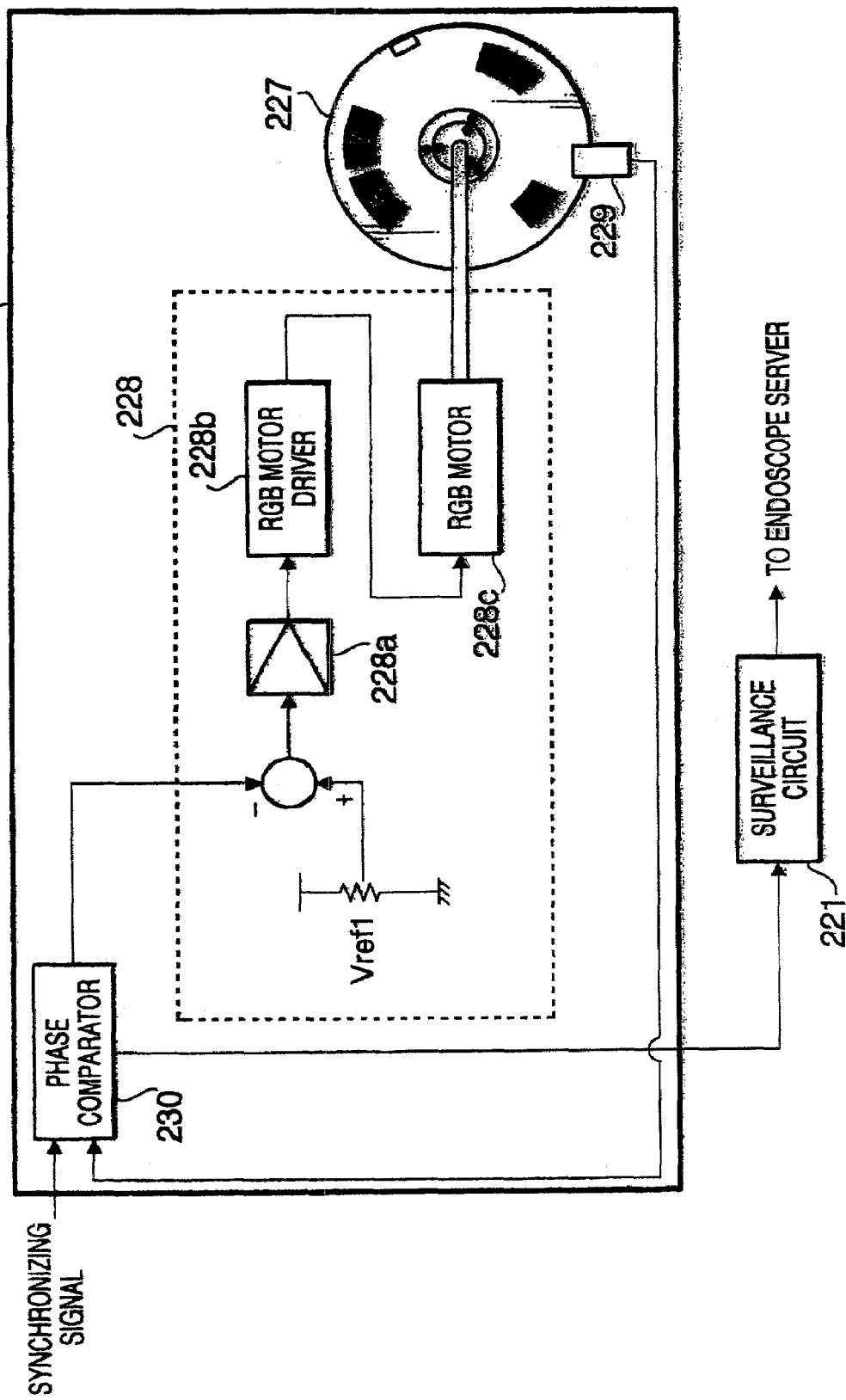
FIG. 9 is a block diagram of a RGB wheel driving mechanism employed in a light source unit of the endoscope processor, according to the first embodiment.

FIG. 9 is a block diagram of an RGB wheel driving mechanism 226 employed in the light source unit 225 of the endoscope processor 220.

The RGB wheel driving mechanism 226 includes, an RGB wheel 227, an RGB motor unit 228, an RGB sensor 229 that detects the rotation speed of the RGB wheel 227, and a phase comparator 230.

To the phase comparator 230, a synchronizing signal output by the timing controller 231 for synchronizing the various circuits and a signal from the RGB sensor 229, which is indicative of the rotation speed of the RGB wheel, are input. Then phase comparator 229 outputs a signal indicative of a difference of the phases of the input signals.

The RGB motor unit 228 includes an amplifier 228a, an RGB motor driver 228b, and an RGB motor 228c. The output signal of the phase comparator 230 is amplified by the amplifier 228a, and is applied to the motor driver 228b which drives the RGB motor 228c.

If, for example, the RGB wheel 227 rotates slightly slower than a synchronized speed, it becomes necessary to increase the rotation speed of the RGB wheel 227. In such a case, the phase comparator 230 compares the synchronizing signal with the output of the sensor 229,and outputs a signal which controls the rotation speed of the RGB motor 228c to increase. If, for example, the RGB wheel 227 rotates slightly faster than a synchronized speed, it becomes necessary to decrease the rotation speed of the RGB wheel 227. In such a case, the phase comparator 230 compares the synchronizing signal with the output of the sensor 229, and outputs a signal which controls the rotation speed of the RGB motor 228c to decrease.

If the operation of the RGB wheel 227 is in irregular condition, the phase comparator 230 outputs a synchronization detection signal. It should be noted that the phase comparator is generally provided with a function of outputting the synchronization detection signal.

Thus, when the synchronization is lost, or the operation is unstable and the synchronized condition frequently lost, the synchronization detection signal becomes active. By applying the synchronization detection signal to the surveillance circuit 221, it becomes possible to examine the normal/irregular status of the RGB wheel 227.

Figure 10:
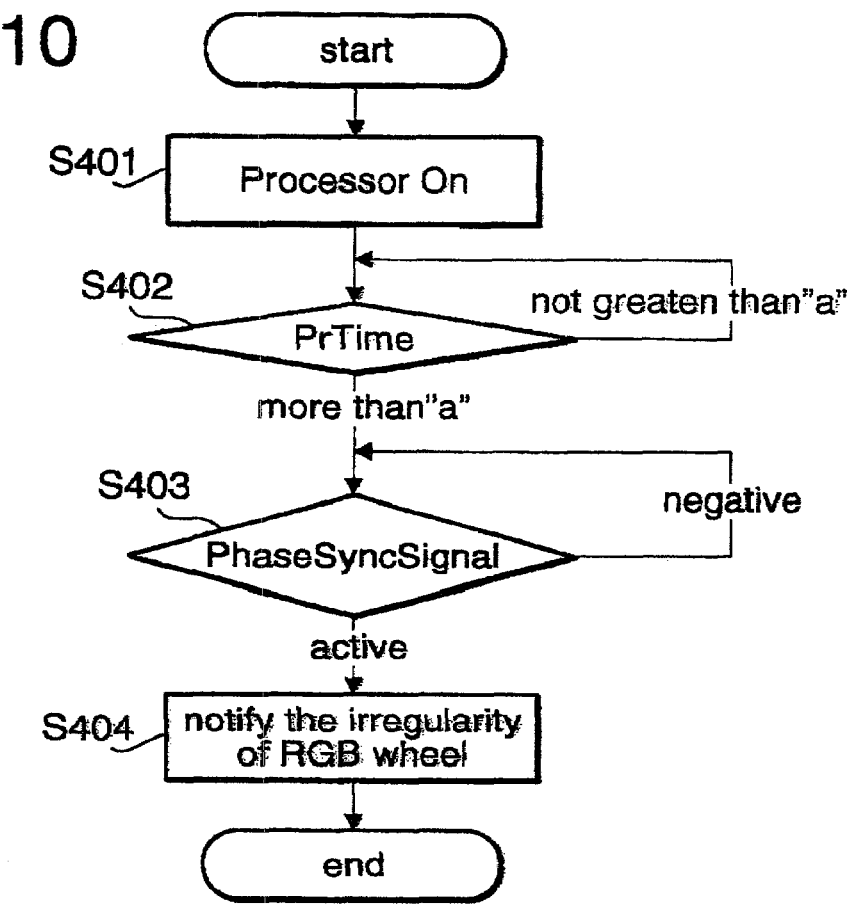
FIG. 10 is a flowchart illustrating an operation examining procedure for the RGB wheel, according to the first embodiment.

FIG. 10 is a flowchart illustrating an operation examining procedure for the RGB wheel 227.

In S401, it is confirmed that the endoscope processor 220 is turned ON. In S402, control repeats a loop for a predetermined period. At the initial stage of turning ON of the endoscope processor 220, the loss of the synchronism may occur. Therefore, by repeating S402, the output of the phase comparator is ignored for a predetermined period of time. Thus, within this period, the loss of the synchronism is not regarded as the irregular condition. That is, if a time period from the turning ON of the endoscope processor 220 is not greater than the predetermined period of time (PrTime), control repeats S402, and if the time period exceeds the predetermined period of time (PrTime), control goes to S403.

In S403, control waits for reception of the synchronization detection signal. That is, S403 is repeated until the synchronization detection signal becomes active. If it becomes active, control goes to S404.

In S404, since the synchronization detection signal has become active, the surveillance circuit 221 detects that the malfunction of the RGB wheel 227 occurs, and transmits a code indicating that the irregular condition occurs to the endoscope server 210.

Figure 11:
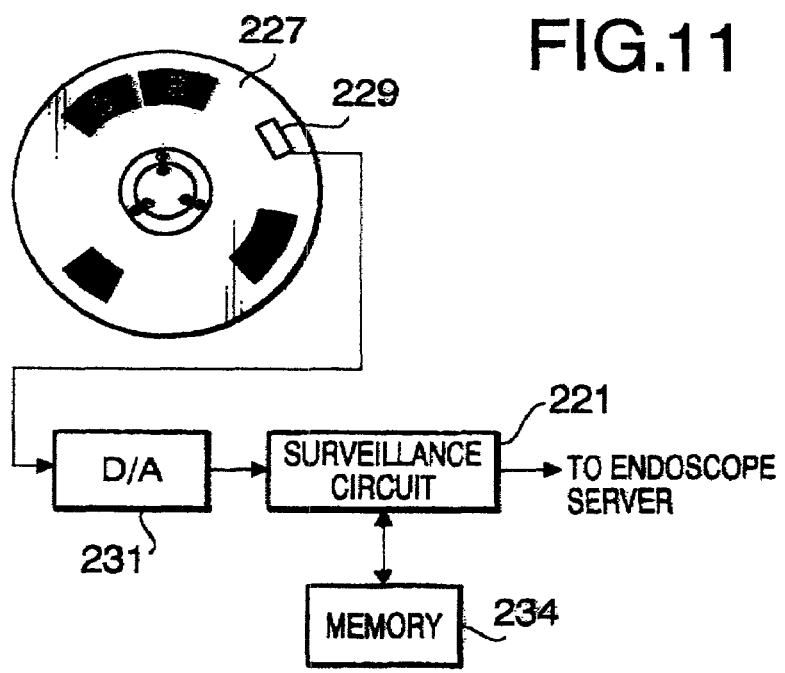
FIG. 11 is a block diagram of an operation examining mechanism that examines the amount of a lamp of the endoscope processor according to the first embodiment.

FIG. 11 is a block diagram of an operation examining mechanism that examines the light amount of a lamp of the endoscope processor.

In this embodiment, the CCD 251 employed in the electronic endoscope 251 is a monochromatic CCD, and the RGB wheel 227 having RGB filters is employed. The RGB filters are arranged at predetermined angular intervals, and sequentially intersect an optical path as the RGB wheel 227 rotates. The lamp (e.g., Xenon lamp) of the light source unit 225 emits so-called white light, which passes through the RGB filters sequentially. With this configuration, the RGB components of light are sequentially directed by the light guide and illuminate an object. The RGB components are sequentially reflected by the object, and the CCD 251 capture the RGB components of the image of the object, which are synthesized to form a color image (i.e., the color image is captured in accordance with a so-called surface sequential method).

Generally, in the electronic endoscope, a frame transfer type CCD, which does not have charge accumulator, is employed for downsizing purpose. When a color image is obtained, in accordance with the surface sequential method, using the frame transfer type CCD, the light receiving surface of the CCD should be shielded for a certain period, during which the accumulated charges are transferred to the endoscope processor. For this purpose, the RGB wheel is configured such that light shielding portions are provided among the RGB filters.

By arranging the RGB sensor 229 on the light shielding portion of the RGB wheel 227, the intensity of the light emitted by the lamp can be detected.

It may be possible to detect the intensity of the light at a timing other than the light shielding periods. However, in such a case, a structure that shields light should be inserted in the optical path in order to detect the intensity, which may lower the intensity of the light directed to the endoscope 250. Therefore, it is preferable that the intensity is detected during the light shielding period.

The output signal of the RGB sensor 229 is D/A converted by the D/A converter 231 and is input to the surveillance circuit 221.

The surveillance circuit 221 examines, based on the output of the RGB sensor 229, whether the light amount of the lamp is appropriate. As described before, if the total operation period after the lamp was exchanged is stored in the memory 234, a warning may be issued so that a used exchange the lamp.

Figure 12:
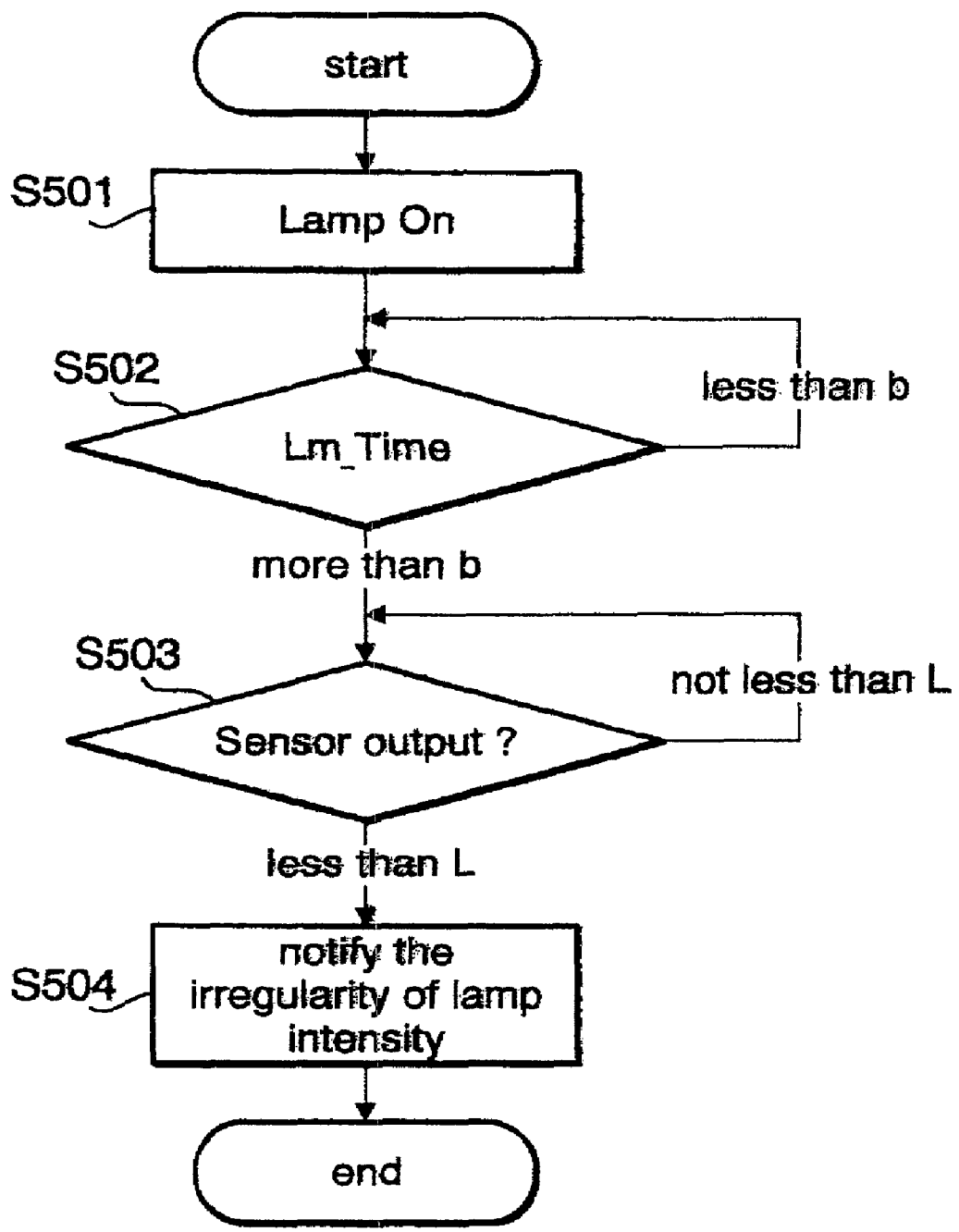
FIG. 12 is a flowchart illustrating an operation examining procedure of the light amount of the lamp, according to the first embodiment.

FIG. 12 is a flowchart illustrating an operation examining procedure of the light amount of the lamp.

In S501, it is confirmed that the lamp is turned ON. Then, in S502, control repeats a loop for a predetermined period (Lm_Time). At the initial stage of turning ON of the lamp, the light amount is unstable. Therefore, by repeating S502, the output of the RGB sensor 229 is ignored for a predetermined period of time. Thus within this period, the low amount of the lamp is not regarded as the irregular condition. That is, if a time period from the turning ON of the lamp is not greater than the predetermined period of time (Lm_Time), control repeats S502, and if the time period exceeds the predetermined period of time (Lm_Time), control goes to S503.

In S503, if the output of the RGB sensor is a predetermined value L or more, control repeats S503. If the output of the RGB sensor 229 is less than the predetermined value L, the light amount of the lamp is less than necessary, and control goes to S504.

In S504, the surveillance circuit 221 transmits a code indicative of an irregular condition of the lamp to the endoscope server 210 since the light amount is too low.

When programs are to be changed, e.g., when control of iris in the endoscope processor 220 and/or hue of color are to be changed, the programs are transmitted from the service server 510 to the endoscope server 210. The endoscope server 210 transmits the programs received from the service server 510 to the controller 235 of each endoscope processor 220. In each endoscope processor 220, the received programs are overwritten on the corresponding programs stored in the system controller 236.

Figure 13:
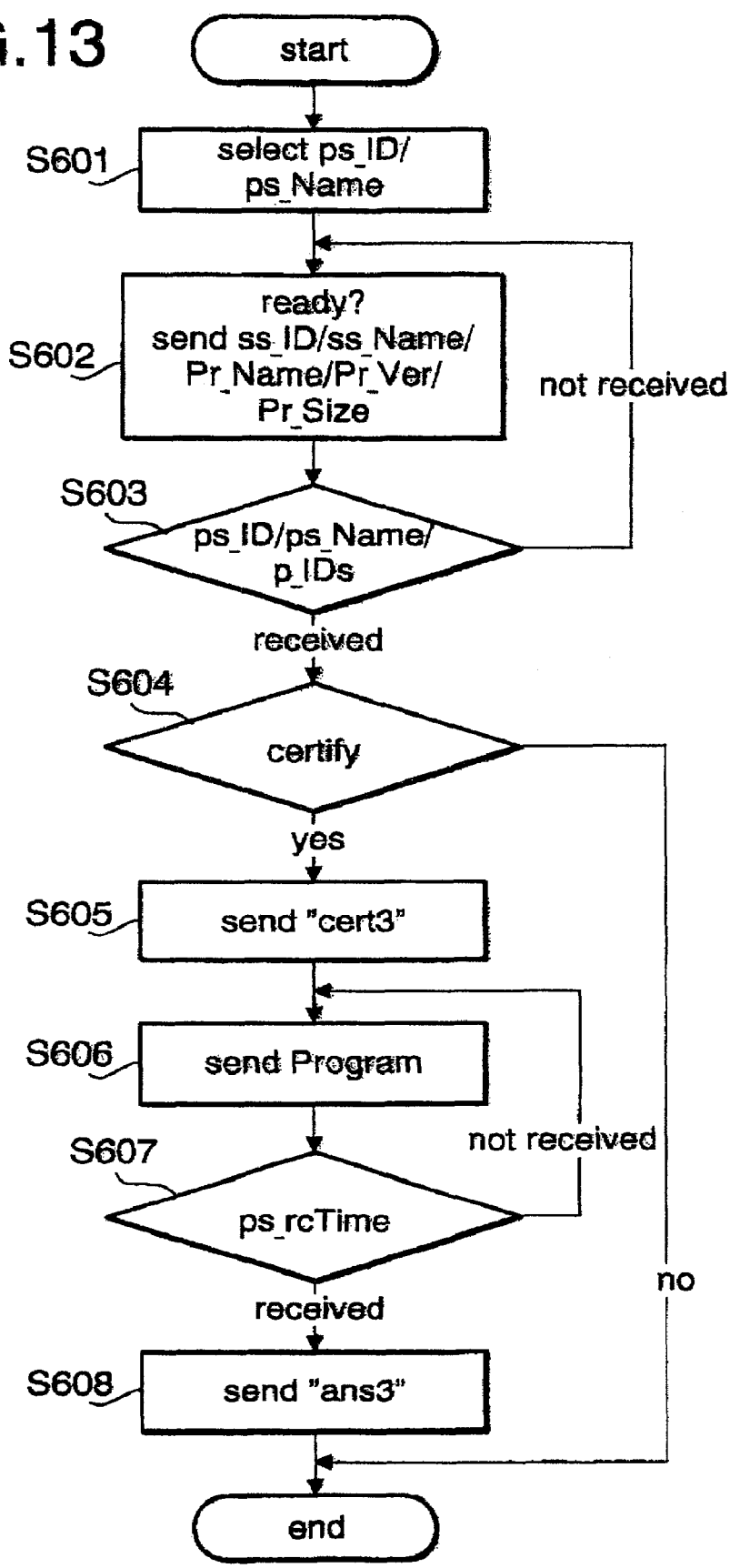
FIG. 13 is a flowchart illustrating a program transmitting procedure of the service server, according to the first embodiment.

FIG. 13 is a flowchart illustrating a program transmitting procedure of the service server 510. In S601, an endoscope server 210 to which the program is to be transmitted is selected. The selection is made by designating the authentication codes (i.e., ps_ID and ps_Name).

In S602, the service server 510 establishes the connection with the endoscope server 210, and transmits the ID (ss_ID), name (ss_Name), the name of the program to be sent (Pr_Name), version information (Pr_Ver) and the size of the program (Pr_Size).

In S603, as a reply from the endoscope server 210, the ID (ps_ID), the name (ps_Name) and the IDs of the connected processors (p_ID) are received and examined. If the data was correctly received (S603:received), control goes to S604. If the data was not receive correctly (S603:not received), control returns to S602.

In S604, authentication of the received data is performed. If the authentication is confirmed (S604:yes), control goes to S605. If the authentication is not confirmed (S604:no), the procedure shown in FIG. 13 is terminated.

In S605, information (cert3) indicating the authentication is confirmed is transmitted to the endoscope server 210. Then, in S606, the service server 510 transmits the new program(s) to the endoscope server 210 of which the authentication is confirmed. In S607, control waits for a reception completion time (ps_rcTime) from the endoscope server 210. If the reception completion time is received (S607:received), control goes to S608. If the reception completion time is not received (S608:not received), control returns to S606.

In S608, a signal (ans3) indicating that the reception completion time is received is transmitted to the endoscope server 210. At this stage, it may be convenient to store the data to form a database.

It may also be convenient if time out periods are set for the loops of S602-S603 and S606-S607, respectively, and if the loops require a longer period than the time out periods, the procedure shown in FIG. 13 is terminated, with a log being recorded.

Figure 14:
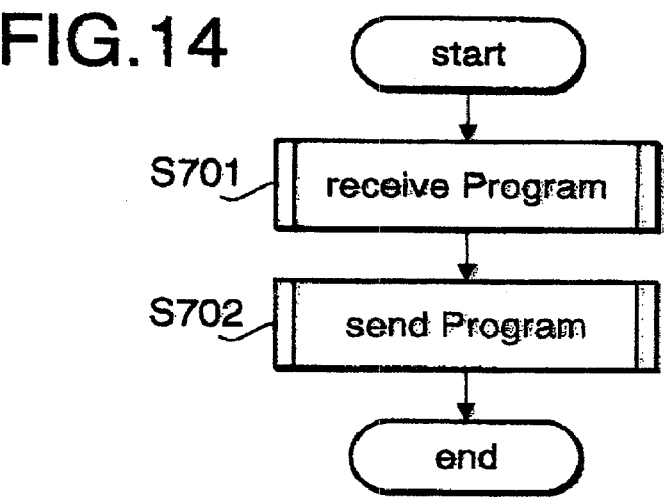
FIG. 14 is a flowchart illustrating a program transmitting/receiving procedure of the endoscope server, according to the first embodiment.

FIG. 14 is a flowchart illustrating a program transmitting/receiving procedure of the endoscope server 210.

In S701, control receives the updated program from the service server 510. In S702, the updated program is transmitted to the controller 235 of the endoscope processor 220.

Figure 15:
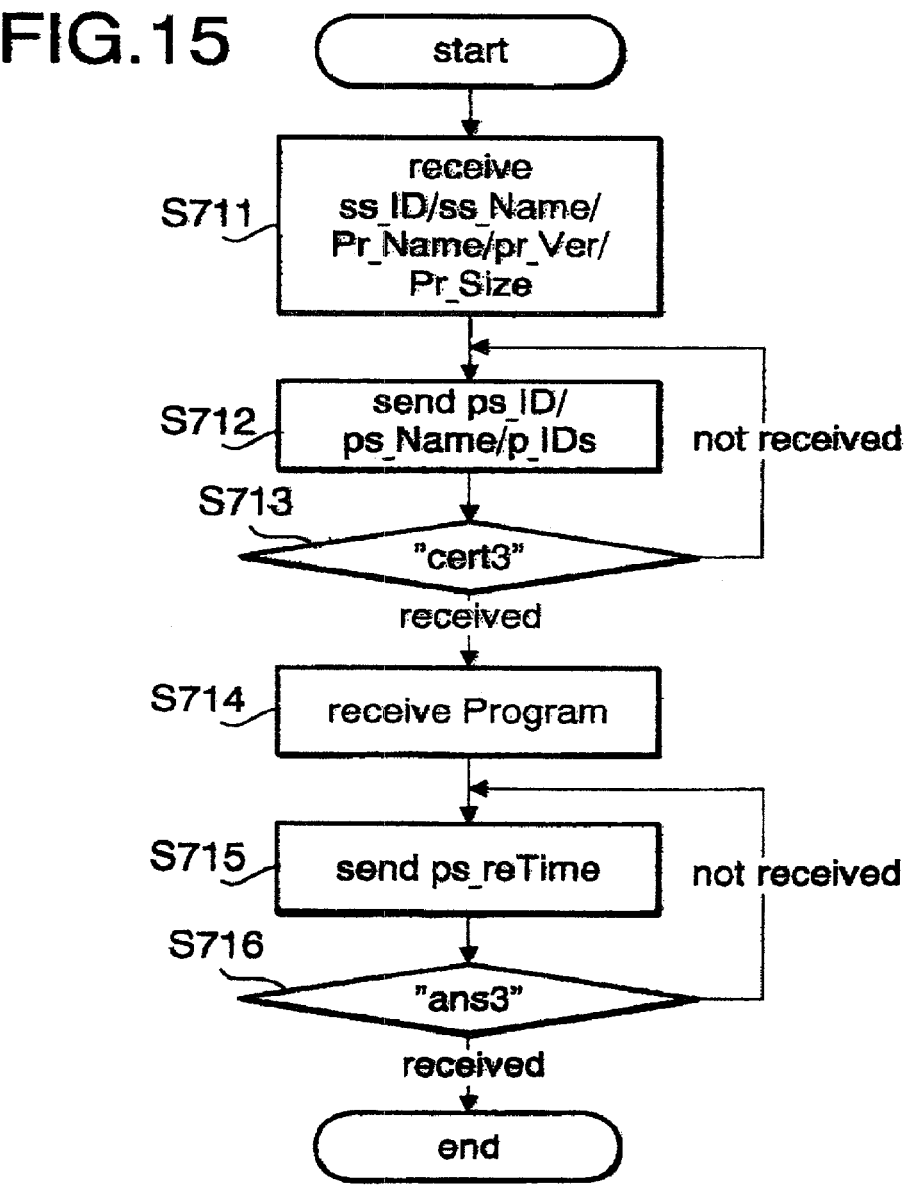
FIG. 15 is a flowchart illustrating the procedure at S701 of FIG. 14.

FIG. 15 is a flowchart illustrating the procedure in S701 of FIG. 14.

In S711, control receives, from the service server 510, the ID (ss_ID), the name (ss_Name), the name of the program to be received (Pr_Name), the version information (Pr_Ver) and the program size (Pr_Size).

In S712, control transmits the ID (ps_ID), the name (ps_Name) and IDs (pIDs) of a plurality of endoscope processors 220 to which the program is transmitted, and the authentication is performed.

In S713, if the authentication code (cert3) is received from the service server 510, control goes to S714. If the authentication code is not received (S713:not received), control returns to S712.

In S714, the updated program is received from the service server 510. In S715, the date and time (ps_retime) when the updated program is received is transmitted to the service server 510.

In S716, if a flow end code (ans3) is received from the service server 510 (S716:received), then the flowchart shown in FIG. 15 is terminated. If the flow end code is not received (S716:not received), control repeats S715 again.

Figure 16:
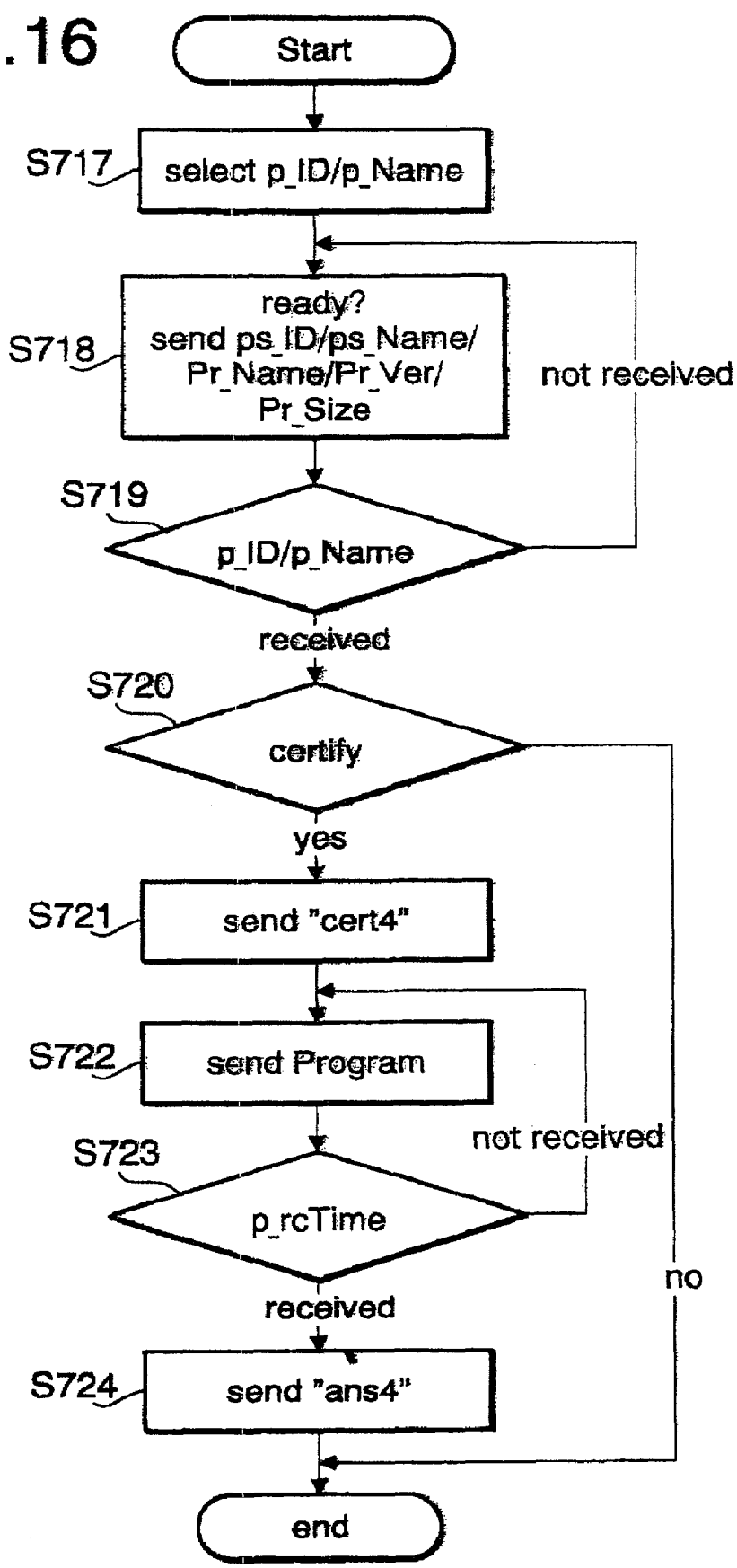
FIG. 16 is a flowchart illustrating the procedure at S702 of FIG. 14.

FIG. 16 is a flowchart illustrating the procedure in S702 of FIG. 14.

In S717, an endoscope processor 220 to which the program is to be transmitted is selected. The selection is made by designating the authentication codes (i.e., p_ID and p_Name).

In S718, the endoscope server 210 establishes the connection with the endoscope processor 220. Further, the endoscope server 210 transmits the ID (ps_ID), the name (ps_Name), the name of the program to be transmitted (Pr_Name), the version information (Pr_Ver) and the size of the program (Pr_Size). Then, control goes to S719.

In S719, as a reply from the endoscope processor 220, the ID (p_ID), the name (p_Name) are received. If the data was correctly received. (S719:received), control goes to S720. If the data was not received correctly (S719:not received), control returns to S718.

In S720, authentication of the data received in S719 is performed. If the authentication is confirmed (S720: yes), control goes to S721. If the authentication is not confirmed (S720:no); the procedure shown in FIG. 16 is terminated.

In S721, information (cert4) indicating the authentication is confirmed is transmitted to the endoscope processor 220. Then, in S722, the endoscope server 210 transmits the new program(s) to the endoscope processor of which the authentication is confirmed. In S723, control waits for a reception completion time (p_rcTime) from the endoscope processor 220. If the reception completion time is received (S723: received), control goes to S724. If the reception completion time is not received (S723:not received), control returns to S722.

In S724, data (ans4) indicating that the data was received is transmitted to the service server 510. It may be convenient to store the data to form a database.

It may also be convenient if time out periods are set for the loops of S712-S713, S715-S716, S718-S719, and S722-S723, respectively, and if the loops require longer periods than the time out periods, the procedure shown in FIG. 16 is terminated, with a log being recorded.

Figure 17:
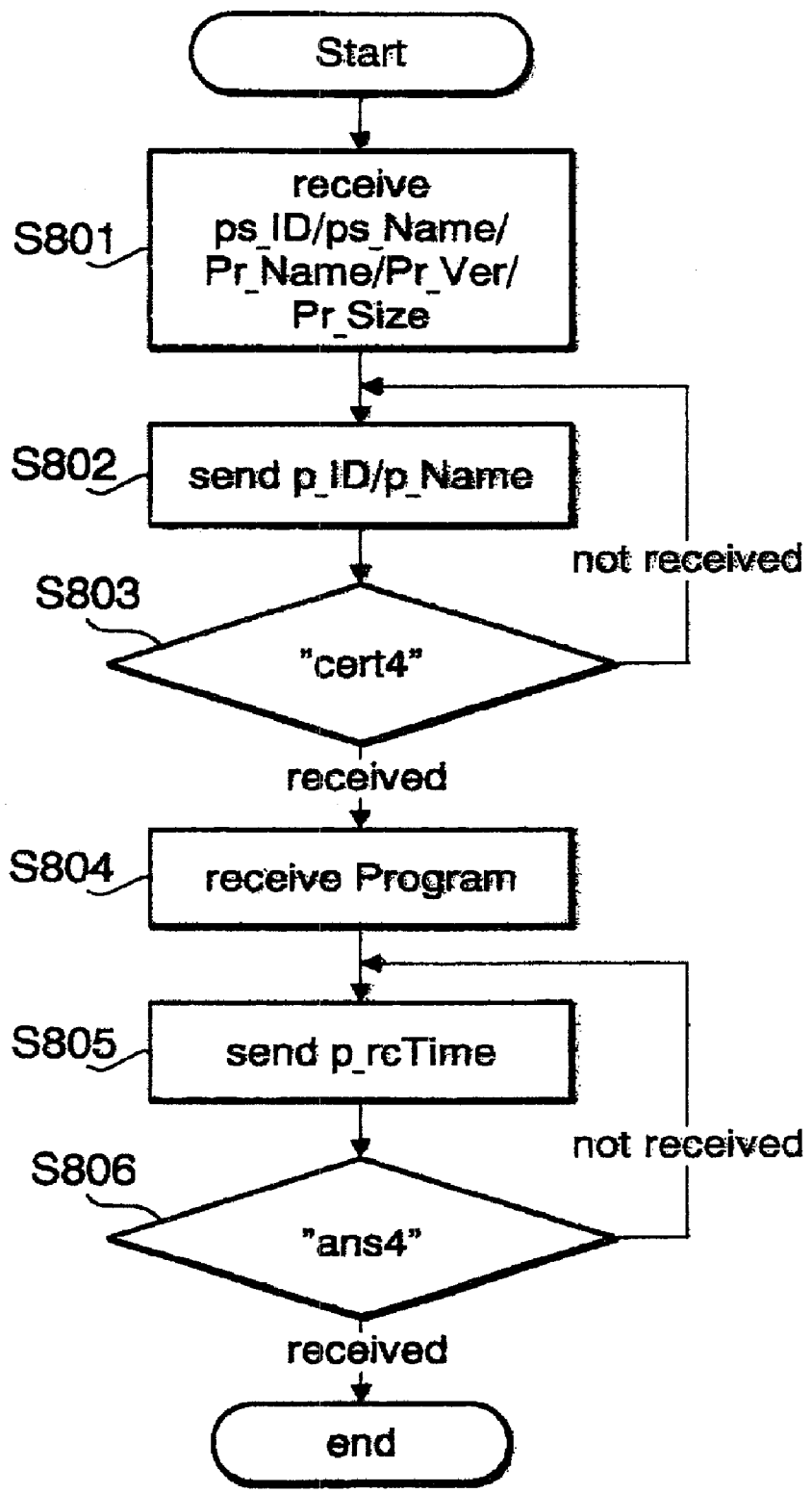
FIG. 17 is a flowchart illustrating a program receiving procedure of the endoscope processor.

FIG. 17 is a flowchart illustrating a program receiving procedure of the endoscope processor 220.

In S801, from the endoscope server 210, the ID (ps_ID), the name (ps_Name), the name of the program to be transmitted (Pr_Name), the version information (Pr_Ver) and the size of the program (Pr_Size) are received. Then, control goes to S802.

In S802, the endoscope processor 220 transmits the ID (p_ID) and the name (p_Name), and the authentication is performed. In S803, if the authentication code (cert4) is received from the endoscope server 210 (S803:received), control goes to S804. If the authentication code is not received (S803:not received), the control goes to S802.

In S804, the updated program is received from the endoscope server 210. Then, in S805, the date and time (p_rcTime) when the program was received are transmitted to the endoscope server 210.

In S806, if the flow end code (ans4) is received from the endoscope server 210 (S806:received), the flowchart shown in FIG. 17 is terminated. If the flow end code is not received (S806:not received), then S805 is repeated.

It may be convenient if time out periods are set for the loops of S802-S803 and S805-S806, respectively, and if the execution of the loops requires longer periods than the time out periods, the procedure shown in FIG. 17 is terminated, with a log being recorded.

Second Embodiment

FIG. 18 schematically shows an entire configuration of an endoscope system 2 according to a second embodiment of the invention.

The endoscope system 2 includes a service server 1510 equipped in a service facility 1500, and at least one endoscope processor 1220 equipped in each of at least one medical facility 1200. The endoscope processor 1220 and the service server 1510 are connected through a communication network 1100 such as the Internet.

When irregular conditions are encountered in the endoscope processor 1220, the endoscope processor 1220 notifies the condition to the service server 1510 through the communication network 1100, in accordance with a predetermined protocol. The service server 1510, when it receives the information indicating that the endoscope processor 1220 is in the irregular condition, displays warning messages or the like on a monitor 1511 of the service server 1510 to notify the same to a service person.

When the above procedure is executed, it is preferable that authentication is performed to avoid the unauthorized access from outside.

When a program controlling an operation of the endoscope processor 1220 is changed, the updated program is sent to each endoscope processor 1220 through the communication network 1100. The endoscope processor 1220 receives the updated program, and operation thereof is changed.

Also in this case, it is preferable that authentication is performed to avoid the unauthorized access from outside.

According to the second embodiment, communication is performed without using the endoscope server. Thus, in a relatively small medical facility such as one having only a single endoscope processor 1220, it becomes unnecessary to implement an endoscope server, which decreases the equipment cost.

FIG. 19 shows a block diagram of the endoscope processor 1220 to which an endoscope is connected. In the second embodiment, inside the endoscope processor 1220, a primary image processing circuit 1222 which converts the image signal output by a CCD (Charge Coupled Device) 1251 into digital data having a predetermined format, and an image memory 1223 which stores the digital data output by the primary image processing circuit 1222, and secondary image signal processing circuit 1224 which converts the digital data stored in the image memory 1223 into a video signal such as an NTSC format video signal.

With this configuration, the image captured by the CCD 1251 provided in the electronic endoscope 1250 can be output as an image displayed on the monitor 1260 and/or an image printed out by a video printer 1261 connected to the endoscope processor 1220.

Further, the endoscope processor 1220 includes a light source unit 1225 which supplies illumination light to a light guide provided in the electronic endoscope 1250, a timing controller 1231 which generates synchronizing signals to be supplied to various circuits, and a system controller 1236 that controls the respective circuits. The endoscope processor 1220 further includes a controller 1235 which is connected with the communication network 1100 to control the endoscope system controller 236.

Using front panel switches 1237, the endoscope processor 1220 can be operated. A power unit 1238 is provided to supply electrical power to the endoscope processor 1220.

The endoscope processor 1220 is provided with a surveillance circuit 1221. The surveillance circuit 1221 examines whether each circuit operates correctly. If the surveillance circuit 1221 detects that an irregular operation is performed, it transmits the authentication thereof and the status of the irregular operation via the communication network 1100. It should be noted that the irregular operation of the endoscope processor 1220 includes, for example, a loss of synchronism of the RGB wheel, insufficient light amount of a lamp of the light source unit 1225.

FIG. 20 is a flowchart illustrating a condition notifying procedure of a service server 1510 according to the second embodiment.

In S901, in the surveillance circuit 1221 of each endoscope processor 1220, a communication with the service server 1510 is established, and the ID number (p_ID) and name (p_Name) are sent for authentication. Then, control proceeds to S902.

In S902, the endoscope processor 1220 waits for reception of an authentication code (cert5) from the service server 1510. If the authentication code (cert5) is received (S902: received), control goes to S903. If the authentication code (cert5) is not received within a predetermined period (S902: not received), control returns to S901.

In S903, a current irregular condition code (Error_Code) and the date and time at which the surveillance circuit 1221 detects the irregular condition are sent to the service server. In S904, control waits for reception of a flow end code (ans5) from the service server 1510. When the flow end code is received (S904:received), control terminates the procedure shown in FIG. 20. If the flow end code is not received within a predetermined period (S904:not received), control returns to S903. It should be noted that, at this stage, the data may be recorded to form a database.

It may be convenient to set a predetermined timeout period for the execution of the procedure shown in FIG. 20, and if the loop of S901 to S902, or the loop of S903 to S904 is repeated for a period longer than the timeout period, the flowchart shown in FIG. 20 is forcibly terminated, with a log being recorded.

FIG. 21 is a flowchart illustrating a condition notifying procedure of the service server 1510, according to the second embodiment. In S1001, control receives the ID number (p_ID) and the name (p_Name) of the endoscope processor 1220 in the irregular condition from the surveillance circuit 1221 of the endoscope processor 1220. In S1002, the communication is established and the authentication is requested based on the transmitted data. If the authentication is confirmed (S1002:yes), control goes to S1003. If the communication is not ready or the authentication is failed (S1002: no), the procedure shown in FIG. 21 is terminated.

In S1003, information (cert5) indicating that the authentication is confirmed is transmitted to the endoscope processor 1220. In S1004, the irregular condition code (Error_Code) and the date and time (p_erTime) at which the surveillance circuit 1221 detects the irregular condition are received. If the data is received in accordance with a predetermined format (S1004: received), control goes to S1005. If the data is not received (S1004: not received), control returns to S1003.

In S1005, control transmits information (ans5) indicating that the data is successfully received to service server 1510. At this stage, the data may be recorded to form a database.

It may be convenient to set a predetermined timeout period for the execution of the procedure shown in FIG. 21, and if the loop of S1003 to S1004 is repeated for a period longer than the timeout period, the flowchart shown in FIG. 21 is forcibly terminated, with a log being recorded.

FIG. 22 is a flowchart illustrating a program transmitting procedure of the service server 1510.

In S1101, an endoscope processor 1220 to which the program is to be transmitted is selected. The selection is made by designating the authentication codes (i.e., ps_ID and ps_Name).

In S1102, the service server 1510 establishes the connection with the endoscope processor 1220, and transmits the ID (ss_ID), name (ss_Name), the name of the program to be sent (Pr_Name), version information (Pr_Ver) and the size of the program (Pr_Size).

In S1103, as a reply from the endoscope processor 1220, the ID (ps_ID) and the name (ps_Name) are received. If the data was correctly received (S1103:received), control goes to S1104. If the data was not received (S1103:not received), control returns to S1102.

In S1104, authentication of the received data is performed. If the authentication is confirmed (S1104:yes), control goes to S1105. If the authentication is not confirmed (S1104:no), the procedure shown in FIG. 22 is terminated.

In S1105, information (cert6) indicating the authentication is confirmed is transmitted to the endoscope processor 1220. Then, in S1106, the service server 1510 transmits the new program(s) to the endoscope processor 1220 of which the authentication is confirmed.

In S1107, control waits for a reception completion time (p_rcTime) from the endoscope processor 1220. If the reception completion time is received (S1107:received), control goes to S1108. If the reception completion time is not received (S1108:not received), control returns to S1106.

In S1108, a signal (ans6) indicating that the reception completion time is received is transmitted to the endoscope processor 1220. At this stage, it may be convenient to store the data to form a database.

It may also be convenient if timeout periods are set for the loops of S1102-S1103 and S1106-S1107, respectively, and if the loops require a longer period than the time out periods, the procedure shown in FIG. 22 is terminated with a log being recorded.

FIG. 23 is a flowchart illustrating a program receiving procedure of the endoscope processor 1220, according to the second embodiment.

In S1201, the endoscope processor 1220 receives from the service server 1510, the ID (ss_ID), the name (ss_Name), the name of the program to be transmitted (Pr_Name), the version information (Pr_Ver), and the program size (Pr_Size).

In S1202, control transmits the ID (ps_ID) and the name (ps_Name), and the authentication is performed.

In S1203, if the authentication code (cert6) is received from the service server 1510 (S1203:received), control goes to S1204. If the authentication code is not received (S123:not received), control returns to S1202.

In S1204, the updated program is received from the service server 1510. In S1205, the date and time (p_rcTime) when the updated program is received is transmitted to the service server 1510.

In S1206, if a flow end code (ans6) is received from the service server 1510 (S1206:received), then the flowchart shown in FIG. 23 is terminated. If the flow end code is not received (S1206:not received), control returns to S1205 again.

It may be convenient if timeout periods are set for the loops of S1202-S1203 and S1205-S1206, respectively, and if the loops require a longer period than the time out periods, the procedure shown in FIG. 23 is terminated, with a log being recorded.

Third Embodiment

FIG. 24 schematically shows an entire configuration of an endoscope system 3 according to a third embodiment of the invention.

The endoscope system 3 includes, a service server 2510 equipped in a service facility 2500, and at least one endoscope processor 2220 equipped in each of at least one medical facility 2200. The endoscope processor 2220 and the service server 2510 are connected via a communication network 2100 such as the Internet.

Each of the endoscope processor 2220 is connected with a microphone 2263 for receiving voice and a video camera 2262 for capturing a video image. With the microphone 2263, and the video camera 2262, the voice and image of a user in the medical facility 2200 can be processed in the endoscope processor 2220. The processed voice and image will be transmitted, in accordance with a predetermined protocol, through the communication network 2100. The image captured by the endoscope which is connected to the endoscope processor 2220 will also be transmitted. Further, the endoscope processor 2220 is capable of processing the audio and video data received through the communication network 2100. The processed audio and video data is output through a speaker 2264 and a display 2260, respectively.

The service server 2510 is also connected with a microphone 2513 and a video camera 2512. The voice and image of a service person in the service facility 2500 can be processed by the service server 2510. The audio/video data can be transmitted, in accordance with a predetermined protocol, through the communication network 2100. Further, the service server 2510 is capable of processing the audio and video data received through the communication network 2100. The processed audio and video data is output through a speaker 2514 and a display 2511, respectively.

With the above configuration, the audio/video data cane be transmitted in both directions. Therefore, when an irregular condition occurs, an operation for updating programs or the like can be performed with confirming the operation procedure via voice and video image.

Preferably, at respective procedures, authentication may be performed to avoid the unauthorized access from outside.

FIG. 25 shows a block diagram of the endoscope processor 2220 to which an endoscope is connected. In the third embodiment, the endoscope processor 2220 includes, a primary image processing circuit 2222 which converts the image signal output by a CCD (Charge Coupled Device) 2251 provided at the distal end of the electronic endoscope 2250 into digital data having a predetermined format, and an image memory 2223 which stores the digital data output by the primary image processing circuit 2222, and secondary image signal processing circuit 2224 which converts the digital data stored in the image memory 2223 into a video signal such as an NTSC format video signal.

With this configuration, the image captured by the CCD 2251 provided in the electronic endoscope 2250 can be output as an image displayed on the monitor 2260 and/or an image printed out by a video printer 2261 connected to the endoscope processor 2220.

Further, the endoscope processor 2220 includes a light source unit 2225 which supplies illumination light to a light guide 2252 provided in the electronic endoscope 2250, a timing controller 2231 which generates synchronizing signals to be supplied to various circuits, and a system controller 2236 that controls the respective circuits. The endoscope processor 2220 further includes a controller 2235 which is connected with the communication network 2100 to communicate with the service server 2510 in order to control the endoscope system controller 2236.

Using front panel switches 2237, the endoscope processor 2220 can be operated. An power unit 2238 is provided to supply electrical power to the endoscope processor 2220.

Further, an image I/O (input/output) circuit 2241 and an audio I/O circuit 2242 are provided in the endoscope processor 2220. The image I/O circuit 2241 processes image signals output by the video camera 2262 and/or the secondary image signal processing circuit 2224, and transmit the processed signals to the service server 2510 through the communication network 2100. As is generally performed in the art, when the image signal is transmitted, various procedures for decreasing the amount of the data may be applied. The image I/O circuit 2241 also receives the image signal transmitted from the service server 2510 through the communication network 2100 and outputs the same to the display 2260 connected to the endoscope processor 2220.

The audio I/O circuit 2242 processes audio signal output by the microphone 2263 and transmits the processed signal to the service server 2510 through the communication network 2100. The audio I/O circuit 2242 also receives the audio signal transmitted from the service server 2510 through the communication network 2100 and outputs the same to the speaker 2264 connected to the endoscope processor 2220.

A light source unit 2225 of the endoscope processor 2220 includes an RGB wheel driving mechanism similar to that of the first embodiment (see FIG. 9). Therefore, by varying the value Vref1 defining the operation of the RGB motor driver, operation of the RGB wheel can be controlled. The value Vref1 is controlled by the system controller 2236. Therefore, by controlling the controller 2236 through the communication network 2100, the operation of the RGB wheel can be remotely controlled by the service server 2510.

For example, when an irregular condition occurs in a medical facility 2200, a service person at the service facility 2500 may view the image of the processor in the irregular condition on a monitor 2511 of the service server 2510, and further, access the controller 2235 and change the value Vref1 to fix the problem.

It is also possible to set the operation of the endoscope processor 2220 at the service server 2510 with monitoring the image thereof. Therefore, if the irregular condition is caused due to erroneous operation of the endoscope processor 2220, a service person may check the operation of the endoscope processor 2220 or fix the problem at the initial stage thereof, only by monitoring an image, without going to the facility at which the endoscope processor 2220 in question is equipped.

The system controller 2236 controls all the circuits inside the endoscope processor 2220, and therefore, the system controller 2236 can change the hue and/or operation of the iris, When there is a problem in the hue and/or operation of the iris in a medical facility, a service person may view the image of the endoscope processor 2220 in the irregular condition on the monitor 2511 of the service server 2510, and by accessing the controller 2235 of the endoscope processor 2220, the setting of the system controller 2236 can be changed.

It is also possible to confirm the operation of an endoscope processor 2220 periodically. For example, a service person may operates the service server 2510 to display the image of the endoscope processor 2220 of which the operation is confirmed, and operation of the endoscope processor 2220 is automatically controlled such that for example, the iris is fully closed/opened, the lamp is turned ON/OFF, the hue is changed, and monitor the image transmitted from the endoscope processor 2220. If there is an irregular condition in the transmitted image and/or the image is too dark and/or it takes too long to turn ON the lamp, the necessity of the maintenance can be decided.

In the above described embodiments, the system is configured such that the endoscope processor performs the surveillance of the endoscope processor itself and/or the endoscope connected to the endoscope processor. However, the invention is not limited to such a configuration. The surveillance may be performed at an external device that is connected to the endoscope processor through a in-facility network or communication network.

Further, the invention is not limited to a case where the endoscope and the endoscope processor are checked/controlled. Any other instrument, such as a display device connected to the endoscope processor or the like may also be subjected to the surveillance.

As described above, according to the endoscope system, maintenance of the system can be performed quickly even if the equipment is located at a remote area from a service server.

Although three embodiments are described separately, various combination, where appropriate, and modification of the embodiments can be achieved without departing from the gist of the invention. For example, the microphone and/or video camera may be employed not only in the third embodiment, but can be employed in any one of the other embodiments.

The present disclosure relates to the subject matter contained in Japanese Patent Application No. 2001-069495, filed on Mar. 12, 2001, which is expressly incorporated herein by reference in its entirety.

What is claimed is:

1. An endoscope system, comprising:
   an endoscope processor that processes an image signal output by an electronic endoscope and outputs a processed image signal to an image outputting system;
   an endoscope controlling system that is connected to said endoscope processor and controls an operation of at least one of said endoscope processor and a device connected to said endoscope processor;
   an endoscope server that communicates with said endoscope controlling system through a first network;
   a service server that communicates with at least one of said endoscope processor and said device connected to said endoscope processor through a second network; and
   a surveillance circuit that surveys an operation of at least one of said endoscope processor and said device connected to said endoscope processor, said surveillance circuit being provided in said endoscope controlling system and configured to detect an irregular condition of at least one of said endoscope processor and said device connected to said endoscope processor,
   said endoscope controlling system transmitting a surveying result of said surveillance circuit to said endoscope server through said first network in response to receiving an authentication code from said endoscope server, said surveying result comprising an irregular condition code,
   said endoscope server transmitting the surveying result of said surveillance circuit to said service server through said second network.

2. The endoscope system according to claim 1, wherein said device connected to said endoscope processor includes said electronic endoscope.

3. The endoscope system according to claim 1, wherein a communication between said service server and said endoscope server is established only when an authentication is confirmed therebetween.

4. The endoscope system according to claim 1, wherein a communication between said endoscope server and said endoscope controlling system is established only when an authentication is confirmed therebetween.

5. The endoscope system according to claim 1,
   at least one of said endoscope processor and said service server including an image input system,
   at least the other of said endoscope processor and said service server including an image output system,
   an image input through said image input system being transmitted to said image output system through said second network.

6. The endoscope system according to claim 1,
   at least one of said endoscope processor and said service server including an audio input system,
   at least the other of said endoscope processor and said service server including an audio output system,
   an audio input through said audio input system being transmitted to said audio output system through said second network.

7. The endoscope system according to claim 1, wherein the first network comprises a local area network and the second network comprises the Internet.

8. An endoscope system, comprising:
   an endoscope processor that processes an image signal output by an electronic endoscope and outputs a processed image signal to an image outputting system;
   an endoscope controlling system that is connected to said endoscope processor and controls an operation of at least one of said endoscope processor and a device connected to said endoscope processor;
   a surveillance circuit configured to detect an irregular condition of at least one of said endoscope processor and said device connected to said endoscope processor;
   an endoscope server that communicates with said endoscope controlling system through a first network, wherein said endoscope controlling system transmits an irregular condition code from said surveillance circuit to said endoscope server in response to receiving an authentication code from said endoscope server; and a service server that communicates with at least one of said endoscope processor and said device connected to said endoscope processor through a second network,
wherein said endoscope controlling system includes:
   a system controller that executes a program controlling operation of said endoscope processor; and
   a controller that controls said system controller to modify the program executed by said system controller,
wherein said service server transmits data used to modify the program to be executed by said system controller to said endoscope server through said second network,
said endoscope server transmits the data transmitted from said service server to said endoscope controlling system through said first network, and
said controller of said endoscope controlling system controls said system controller to modify the program to be executed by said system controller in accordance with the data transmitted from said endoscope server.

9. The endoscope system according to claim 8, wherein said device connected to said endoscope processor includes said electronic endoscope.

10. The endoscope system according to claim 8, wherein a communication between said service server and said endoscope server is established only when an authentication is confirmed therebetween.

11. The endoscope system according to claim 8, wherein a communication between said endoscope server and said endoscope controlling system is established only when an authentication is confirmed therebetween.

12. The endoscope system according to claim 8, wherein said endoscope processor includes said endoscope controlling system.

13. The endoscope system according to claim 8,
at least one of said endoscope processor and said service server including an image input system,
at least the other of said endoscope processor and said service server including an image output system,
an image input through said image input system being transmitted to said image output system through said second network.

14. The endoscope system according to claim 8,
at least one of said endoscope processor and said service server including an audio input system,
at least the other of said endoscope processor and said service server including an audio output system,
an audio input through said audio input system being transmitted to said audio output system through said second network.

15. The endoscope system according to claim 8, wherein the first network comprises a local area network and the second network comprises the Internet.

* * * * *